United States Patent
Ikeda et al.

(10) Patent No.: US 9,933,701 B2
(45) Date of Patent: Apr. 3, 2018

(54) PHOTOBASE GENERATOR

(71) Applicant: SAN APRO LTD., Kyoto-shi, Kyoto (JP)

(72) Inventors: Takuya Ikeda, Kyoto (JP); Atsushi Shiraishi, Kyoto (JP)

(73) Assignee: SAN APRO LTD., Kyoto (JP)

( * ) Notice: Subject to any disclaimer, the term of this patent is extended or adjusted under 35 U.S.C. 154(b) by 5 days.

(21) Appl. No.: 15/100,503

(22) PCT Filed: Nov. 17, 2014

(86) PCT No.: PCT/JP2014/005755
§ 371 (c)(1),
(2) Date: May 31, 2016

(87) PCT Pub. No.: WO2015/083331
PCT Pub. Date: Jun. 11, 2015

(65) Prior Publication Data
US 2016/0299429 A1   Oct. 13, 2016

(30) Foreign Application Priority Data
Dec. 4, 2013   (JP) .................................. 2013-250937

(51) Int. Cl.
| | | |
|---|---|---|
| G03F 7/004 | (2006.01) | |
| C07F 5/02 | (2006.01) | |
| C07F 9/06 | (2006.01) | |
| C07C 279/04 | (2006.01) | |
| C07D 487/04 | (2006.01) | |
| C07F 9/572 | (2006.01) | |
| C07D 233/54 | (2006.01) | |
| C07D 335/16 | (2006.01) | |
| C07D 409/06 | (2006.01) | |
| G03F 7/038 | (2006.01) | |
| C07D 233/58 | (2006.01) | |
| C07D 233/60 | (2006.01) | |

(52) U.S. Cl.
CPC .......... *G03F 7/0045* (2013.01); *C07C 279/04* (2013.01); *C07D 233/54* (2013.01); *C07D 233/58* (2013.01); *C07D 233/60* (2013.01); *C07D 335/16* (2013.01); *C07D 409/06* (2013.01); *C07D 487/04* (2013.01); *C07F 5/02* (2013.01); *C07F 5/027* (2013.01); *C07F 9/065* (2013.01); *C07F 9/5721* (2013.01); *G03F 7/038* (2013.01)

(58) Field of Classification Search
CPC ........ C07F 5/027; C07F 9/065; C07F 9/5721; G03F 7/0382; G03F 7/0045; C07C 279/04
USPC .......................................... 430/270.1; 568/6
See application file for complete search history.

(56) References Cited

U.S. PATENT DOCUMENTS

| 6,489,374 B1 | 12/2002 | Baudin et al. | |
|---|---|---|---|
| 2012/0264056 A1* | 10/2012 | Lin ........................ | G03F 7/075 430/281.1 |

FOREIGN PATENT DOCUMENTS

| JP | 10-7709 A | 1/1998 |
|---|---|---|
| JP | 10-152548 A | 6/1998 |
| JP | 10-197984 A | 7/1998 |
| JP | 10-319585 A | 12/1998 |
| JP | 2000-143685 A | 5/2000 |
| JP | 2002-523393 A | 7/2002 |
| JP | 2002-226487 A | 8/2002 |
| JP | 2004-198781 A | 7/2004 |
| JP | 2005-107235 A | 4/2005 |
| JP | 2005-264156 A | 9/2005 |
| JP | 2007-119766 A | 5/2007 |
| JP | 2007-187924 A | 7/2007 |
| JP | 2009-244745 A | 10/2009 |
| JP | 2009-280785 A | 12/2009 |
| JP | 2012-168526 A | 9/2012 |
| WO | 2005/014696 A1 | 2/2005 |
| WO | 2009/122664 A1 | 10/2009 |

OTHER PUBLICATIONS

International Search Report dated Feb. 3, 2015, issued in counterpart Intenational Application No. PCT/JP2014/005755 (3 pages).
Suyama et al., "Quaternary Ammonium Salt as DBU-Generating Photobase Generator", Journal of Photopolymer Science and Technology, vol. 19, No. 1, 2006, pp. 81-84, Cited in Specification.

* cited by examiner

*Primary Examiner* — John S Chu
(74) *Attorney, Agent, or Firm* — Westerman, Hattori, Daniels & Adrian, LLP

(57) ABSTRACT

Provided are a photobase generator having higher sensitivity to light than do conventional photobase generators, and a photosensitive resin composition containing the photobase generator. The present invention is a photobase generator characterized in containing a salt represented by general formula (1). (In formula (1), $R^1$-$R^4$ are mutually independent groups represented by general formula (2), C1-18 alkyl groups, or Ar, with at least one being a group represented by general formula (2); in formula (2), (D) is a divalent group bonded on at least one side to elemental boron, and $Ar^1$ is the same as the aforementioned Ar; and $Q^+$ is a monovalent onium cation.)

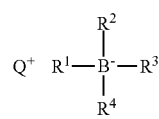

(1)

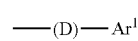

(2)

9 Claims, No Drawings

PHOTOBASE GENERATOR

TECHNICAL FIELD

The present invention relates to a photobase generator generating a base by photoirradiation. More particularly, the present invention relates to a photobase generator suitably used for the production of a material to be cured by utilizing a base generated by photoirradiation (for example, a coating agent or a coating material) or a product or a member formed after being subjected to patterning in which the difference in solubility to a developing solution between the exposed part and the unexposed part is utilized (for example, an electronic component, an optical product, a forming material for an optical component, a layer forming material or an adhesive agent).

BACKGROUND ART

As a photobase generator generating a base by being subjected to exposure, there have been known various photobase generators such as photobase generators generating primary amines or secondary amines and photobase generators generating a strong base (tertiary amines, pKa 8 to 11) and a super-strong base (guanidine, amidine and the like, pKa 11 to 13) (Patent Documents 1 to 7, Non-Patent Documents 1 to 2 and the like).

However, with regard to the photobase generators described in Patent Document 1 and Non-Patent Document 1, the basicity of the base generated is low (pKa<8), and the photobase generator is not suitable as the catalyst for a polymerization reaction or for a crosslinking reaction because the activity is low. Moreover, since these amines have an active hydrogen atom, there has been a problem that a large amount of the photobase generator is required for allowing the reaction to proceed sufficiently because these amines themselves react with one another when used in a polymerization reaction or a crosslinking reaction of epoxides and isocyanates.

Moreover, the base generators described in Patent Documents 2 to 5 and Non-Patent Document 2 and the like have a problem that the performance is low when used as photo-latent base catalysts in a polymerization reaction or a crosslinking reaction of epoxides and isocyanates since the activity to light is low, and moreover, the base generator exerts a low effect when used in combination with a photosensitizer.

Under such circumstances, there has been desired the development of a photobase generator having a catalytic activity for sufficiently curing an epoxy resin, namely, a photobase generator in which the sensitivity to light is more enhanced compared with conventional photobase generators.

PRIOR ART DOCUMENTS

Patent Documents

Patent Document 1: JP-A-10-7709
Patent Document 2: JP-A-2005-107235
Patent Document 3: JP-A-2005-264156
Patent Document 4: JP-A-2007-119766
Patent Document 5: JP-A-2009-280785
Patent Document 6: WO 2005/014696 A
Patent Document 7: WO 2009/122664 A Non-Patent Documents Non-Patent Document 1: Dictionary of Optical Application Technologies and Materials, published by Sangyo-Gijutsu Service Center Co., Ltd., 2006, p. 130
Non-Patent Document 2: J. Photopolym. Sci. Tech., Vol. 19, No. 1 (81) 2006

SUMMARY OF THE INVENTION

Problems to be Solved by the Invention

The problem to be solved by the present invention is to provide a photobase generator which has higher sensitivity to light compared with conventional photobase generators, and a photosensitive resin composition which contains the base generator.

Solutions to the Problems

The present inventors have conducted intensive researches in view of solving said problems, and as a result, have found a photobase generator having excellent characteristics.

That is, the present invention is directed to a photobase generator comprising a salt represented by general formula (1).

[Chemical Formula 1]

[In formula (1), $R^1$ to $R^4$ independently represent a group represented by general formula (2) below, an alkyl group having 1 to 18 carbon atoms or Ar, wherein at least one of $R^1$ to $R^4$ represents a group represented by general formula (2) below, Ar represents an aryl group having 6 to 14 carbon atoms (excluding carbon atoms contained in a substituent as mentioned below), some of hydrogen atoms in the aryl group may be independently substituted by an alkyl group having 1 to 18 carbon atoms, an alkenyl group having 2 to 18 carbon atoms, an alkynyl group having 2 to 18 carbon atoms, an aryl group having 6 to 14 carbon atoms, a nitro group, a hydroxyl group, a cyano group, an alkoxy group or aryloxy group represented by $-OR^{39}$, an acyl group represented by $R^{40}CO-$, an acyloxy group represented by $R^{41}COO-$, an alkylthio group or arylthio group represented by $-SR^{42}$, an amino group represented by $-NR^{43}R^{44}$, or a halogen atom, $R^{39}$ to $R^{42}$ independently represent an alkyl group having 1 to 8 carbon atoms or an aryl group having 6 to 14 carbon atoms, and $R^{43}$ and $R^{44}$ independently represent a hydrogen atom, an alkyl group having 1 to 8 carbon atoms or an aryl group having 6 to 14 carbon atoms; in formula (2), (D) represents a divalent group having at least one bond through which a boron element is bonded, and $Ar^1$ is the same as the above-mentioned Ar, and $Q^+$ represents a monovalent onium cation.]

[Chemical Formula 2]

(2)

Furthermore, the present invention is directed to a photocurable composition comprising the above-described photobase generator and a basic reactive compound.

Furthermore, the present invention is directed to a cured product obtained by curing the above-mentioned photocurable composition.

Effects of the Invention

The photobase generator according to the present invention is sensitive to light and is capable of efficiently generating amines (tertiary amines, amidine, guanidine and the like) which are high in catalytic activity.

Moreover, since the photobase generator according to the present invention does not contain halogen ions and the like as counter anions, there is no fear of metal corrosion.

Moreover, since the photobase generator according to the present invention has no basicity before subjected to exposure, even when contained in a reactive composition, there is no possibility that the storage stability of the reactive composition is lowered.

Moreover, the photobase generator according to the present invention is stable also against heat and hardly generates a base even when heated as long as the photobase generator is not irradiated with light.

Moreover, according to a production method of a cured material prepared with the photocurable composition according to the present invention, by using the above-mentioned photobase generator and irradiating the photobase generator with light, it is possible to efficiently generate amines (tertiary amines, amidine, guanidine and the like) which are high in catalytic activity and to efficiently produce a cured material.

MODE FOR CARRYING OUT THE INVENTION

Hereinafter, an embodiment of the present invention will be described in detail.

A photobase generator refers to such a substance that its chemical structure is decomposed by photoirradiation, so that it generates a base (amine). The base generated is capable of acting as a catalyst for a curing reaction of an epoxy resin, a curing reaction of a polyimide resin, a urethanization reaction between an isocyanate and a polyol, a crosslinking reaction of an acrylate, and the like.

A photobase generator according to the present invention is characterized by containing a salt represented by general formula (1).

[Chemical Formula 3]

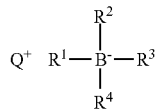
(1)

[In formula (1), $R^1$ to $R^4$ independently represent a group represented by general formula (2) below, an alkyl group having 1 to 18 carbon atoms or Ar, wherein at least one of $R^1$ to $R^4$ represents a group represented by general formula (2) below, Ar represents an aryl group having 6 to 14 carbon atoms (excluding carbon atoms contained in a substituent as mentioned below), some of hydrogen atoms in the aryl group may be independently substituted by an alkyl group having 1 to 18 carbon atoms, an alkenyl group having 2 to 18 carbon atoms, an alkynyl group having 2 to 18 carbon atoms, an aryl group having 6 to 14 carbon atoms, a nitro group, a hydroxyl group, a cyano group, an alkoxy group or aryloxy group represented by —$OR^{39}$, an acyl group represented by $R^{40}CO$—, an acyloxy group represented by $R^{41}COO$—, an alkylthio group or arylthio group represented by —$SR^{42}$, an amino group represented by —$NR^{43}R^{44}$, or a halogen atom, $R^{39}$ to $R^{42}$ independently represent an alkyl group having 1 to 8 carbon atoms or an aryl group having 6 to 14 carbon atoms, and $R^{43}$ and $R^{44}$ independently represent a hydrogen atom, an alkyl group having 1 to 8 carbon atoms or an aryl group having 6 to 14 carbon atoms; in formula (2), (D) represents a divalent group having at least one bond through which a boron element is bonded, and $Ar^1$ is the same as the above-mentioned Ar, and $Q^+$ represents a monovalent onium cation.]

In general formula (1), examples of the alkyl group having 1 to 18 carbon atoms as each of $R^1$ to $R^4$ include linear alkyl groups (methyl, ethyl, n-propyl, n-butyl, n-pentyl, n-octyl, n-decyl, n-dodecyl, n-tetradecyl, n-hexadecyl, n-octadecyl and the like), branched alkyl groups (isopropyl, isobutyl, sec-butyl, tert-butyl, isopentyl, neopentyl, tert-pentyl, isohexyl, 2-ethylhexyl, 1,1,3,3-tetramethylbutyl and the like), cycloalkyl groups (cyclopropyl, cyclobutyl, cyclopentyl, cyclohexyl and the like) and bridged cyclic alkyl groups (norbornyl, adamantyl, pinanyl and the like).

Among these, preferred are a linear or branched alkyl group having 1 to 8 carbon atoms and a cycloalkyl group, and further preferred are a linear alkyl group having 2 to 8 carbon atoms, a branched alkyl group having 3 to 8 carbon atoms and a cycloalkyl group having 5 to 6 carbon atoms.

In general formula (1), examples of the aryl group having 6 to 14 carbon atoms (excluding carbon atoms contained in a substituent as mentioned below) as each of $R^1$ to $R^4$ include monocyclic aryl groups (phenyl and the like), condensed polycyclic aryl groups (naphthyl, anthryl, phenanthryl, anthraquinonyl, fluorenyl, naphthoquinonyl and the like) and aromatic heterocyclic hydrocarbon groups (monocyclic heterocycles such as thienyl, furyl, pyranyl, pyrrolyl, oxazolyl, thiazolyl, pyridyl, pyrimidinyl and pyrazinyl; and condensed polycyclic heterocycles such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, coumarinyl, dibenzothienyl, xanthonyl, thioxanthonyl and dibenzofuranyl).

Beside the groups listed above, examples of the aryl group may include aryl groups in which some of hydrogen atoms in the aryl groups are independently substituted by an alkyl group having 1 to 18 carbon atoms, an alkenyl group having 2 to 18 carbon atoms, an alkynyl group having 2 to 18 carbon atoms, an aryl group having 6 to 14 carbon atoms, a nitro group, a hydroxyl group, a cyano group, an alkoxy group or aryloxy group represented by —$OR^{39}$, an acyl group represented by $R^{40}CO$—, an acyloxy group represented by $R^{41}COO$—, an alkylthio group or arylthio group represented by —$SR^{42}$, an amino group represented by —$NR^{43}R^{44}$, or a halogen atom.

Among these, preferred are phenyl, naphthyl, anthryl, phenanthryl, anthraquinonyl, xanthenyl, thianthrenyl, phenoxathiinyl, chromanyl, isochromanyl, coumarinyl, xanthonyl and thioxanthonyl, and further preferred are phenyl, naphthyl, anthryl and phenanthryl.

In the above-mentioned substituent, examples of the alkenyl group having 2 to 18 carbon atoms include linear or branched alkenyl groups (vinyl, allyl, 1-propenyl, 2-propenyl, 1-butenyl, 2-butenyl, 3-butenyl, 1-methyl-1-propenyl, 1-methyl-2-propenyl, 2-methyl-1-propenyl, 2-methyl-2-propenyl and the like), cycloalkenyl groups (2-cyclohexenyl, 3-cyclohexenyl and the like) and arylalkenyl groups (styryl, cinnamyl and the like).

In the above-mentioned substituent, examples of the alkynyl group having 2 to 18 carbon atoms include linear or branched alkynyl groups (ethynyl, 1-propynyl, 2-propynyl, 1-butynyl, 2-butynyl, 3-butynyl, 1-methyl-2-propynyl, 1,1-dimethyl-2-propynyl, 1-pentynyl, 2-pentynyl, 3-pentynyl, 4-pentynyl, 1-methyl-2-butynyl, 3-methyl-1-butynyl, 1-decynyl, 2-decynyl, 8-decynyl, 1-dodecynyl, 2-dodecynyl, 10-dodecynyl and the like) and arylalkynyl groups (phenylethynyl and the like). Beside the groups listed above, examples of the alkynyl group may include substituted alkynyl groups in which some of hydrogen atoms in the alkynyl groups are independently substituted by a nitro group, a cyano group, a halogen atom, an alkoxy group having 1 to 18 carbon atoms and/or an alkylthio group having 1 to 18 carbon atoms, or the like.

In the above-mentioned substituent, examples of each of $R^{39}$ to $R^{42}$ of an alkoxy group represented by $—OR^{39}$, an acyl group represented by $R^{40}CO—$, an acyloxy group represented by $R^{41}COO—$, an alkylthio group represented by $—SR^{42}$, and an amino group represented by $—NR^{43}R^{44}$ include an alkyl group having 1 to 8 carbon atoms, and specifically, examples thereof include an alkyl group having 1 to 8 carbon atoms among the above-mentioned alkyl groups.

In the above-mentioned substituent, examples of each of $R^{39}$ to $R^{42}$ of an aryloxy group represented by $—OR^{39}$, an acyl group represented by $R^{40}CO—$, an acyloxy group represented by $R^{41}COO—$, an arylthio group represented by $—SR^{42}$, and an amino group represented by $—NR^{43}R^{44}$ include an aryl group having 6 to 14 carbon atoms, and specifically, examples thereof include the above-mentioned aryl groups having 6 to 14 carbon atoms.

Examples of the alkoxy group represented by $—OR^{39}$ include methoxy, ethoxy, n-propoxy, iso-propoxy, n-butoxy, sec-butoxy, tert-butoxy, n-pentoxy, iso-pentoxy, neo-pentoxy, 2-methylbutoxy and the like.

Examples of the aryloxy group represented by $—OR^{39}$ include phenoxy, naphthoxy and the like.

Examples of the acyl group represented by $R^{40}CO—$ include acetyl, propanoyl, butanoyl, pivaloyl, benzoyl and the like.

Examples of the acyloxy group represented by $R^{41}COO—$ include acetoxy, butanoyloxy, benzoyloxy and the like.

Examples of the alkylthio group represented by $—SR^{42}$ include methylthio, ethylthio, butylthio, hexylthio, cyclohexylthio and the like.

Examples of the arylthio group represented by $—SR^{42}$ include phenylthio, naphthylthio and the like.

Examples of the amino group represented by $—NR^{43}R^{44}$ include methylamino, ethylamino, propylamino, dimethylamino, diethylamino, methylethylamino, dipropylamino, dipropylamino, piperidino and the like.

Examples of the halogen atom include a fluorine atom, a chlorine atom, a bromine atom, an iodine atom and the like.

Among these substituents, from the viewpoint of solvent solubility of a salt, preferred are alkoxy groups such as methoxy, ethoxy and n-butoxy, aryloxy groups such as phenoxy and naphthoxy, alkylthio groups such as methylthio, ethylthio and butylthio, arylthio groups such as phenylthio and naphthylthio, a fluorine atom, a chlorine atom and a bromine atom.

General formula (2) below represents a group having at least one bond through which a boron element is bonded.

[Chemical Formula 4]

$$-(D)-Ar^1 \qquad (2)$$

In general formula (2), examples of $Ar^1$ include ones that are the same as those described for the above-mentioned Ar.

Among the examples of $Ar^1$, from the viewpoint of photodecomposability, preferred is one having an absorption peak at a longer wavelength side in the case where respective maximum absorption wavelengths which the above-mentioned Ar and $Ar^1$ have are compared, or it is preferred that respective molar extinction coefficients ($\epsilon$s) to a specific wavelength of the above-mentioned Ar and $Ar^1$ satisfy the relationship of $\epsilon(Ar^1) > \epsilon(Ar)$ when compared. In this context, the maximum absorption wavelength refers to the maximum absorption wavelength at which the molar extinction coefficient is 50 or more in a UV absorption spectrum which each of Ar and $Ar^1$ has. The specific wavelength refers to a wavelength which a light ray emitted from a light source has, and for example, in the case of a light source which emits a light ray of a single wavelength such as an LED light source, respective molar extinction coefficients ($\epsilon$s) to the wavelength thereof are compared. In the case of a light source for a high pressure mercury lamp, wavelengths of the effectively utilizable light ray are i-line (365 nm) and g-line (436 nm), and respective molar extinction coefficients ($\epsilon$s) to the wavelength thereof are compared.

Specific examples of $Ar^1$ preferably include one with a structure selected from known (JP-A-11-279212, JP-A-09-183960 and the like) ones as photosensitizers.

Preferred examples of the combination of Ar and $Ar^1$ include phenyl.anthryl, phenyl.anthraquinonyl, phenyl.thioxanthonyl, phenyl.benzoquinonyl, phenyl.naphthoquinonyl, phenyl.pyrenyl, phenyl.perirenyl, phenyl.tetracenyl, phenyl.phenothiazinyl, phenyl.xanthonyl, phenyl.4-benzoyl-phenylthiophenyl, phenyl.carbazolyl, phenyl.chrysenyl, phenyl.phenanthryl, naphthyl.anthryl, naphthyl.xanthonyl and the like.

In general formula (2), (D) represents a divalent group that bonds a boron element and the above-mentioned $Ar^1$, and specifically, examples thereof include groups selected from the group of an ether, a sulfide, a ketone, an imine, a sulfoxide, a sulfone, an amide, an imide, a carboxylic acid ester, a thiocarboxylic acid ester, a carbonate ester, an acid anhydride, a urea, a thiourea, an acetal, a thioacetal, a carbodiimide, a carbamoyl, a thiocarbamoyl, a silylene and a siloxy, as well as an alkylene having 1 to 18 carbon atoms which may have a substituent, an alkenylene having 2 to 18 carbon atoms, an alkynylene having 2 to 18 carbon atoms, and an arylene having 6 to 14 carbon atoms which may contain a hetero atom.

Among the examples of (D), preferred are an alkylene having 1 to 18 carbon atoms, an arylene with 6 to 14 carbon atoms which may contain a hetero atom, ether, a sulfide and a carboxylic acid ester.

In general formula (1), $Q^+$ represents a monovalent onium cation. Examples of the monovalent onium cation include a known one, and specifically, examples thereof include an oxonium cation, a sulfonium cation, an ammonium cation, a phosphonium cation, and the like. From the viewpoint of being utilized for a reaction in which a base generated by photoirradiation is used as a catalyst, preferred are an ammonium cation and a phosphonium cation, more preferred is an ammonium cation in view of the degree of basicity thereof, and further preferred is E-Y$^+$ and the whole salt thereof is represented by general formula (3).

[Chemical Formula 5]

(3)

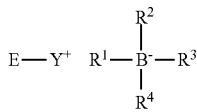

[In formula (3), Y$^+$ represents an ammonio group represented by any one of general formulas (4) to (6) and (8) below; in formula (4), R$^5$ to R$^8$ independently represent a hydrogen atom, an alkyl group having 1 to 18 carbon atoms, an alkenyl group having 2 to 18 carbon atoms or an aryl group having 6 to 14 carbon atoms, and may be bonded to one another to form a ring structure; in formula (5), R$^9$ to R$^{15}$ independently represent a hydrogen atom, an alkyl group having 1 to 18 carbon atoms, an alkenyl group having 2 to 18 carbon atoms or an aryl group having 6 to 14 carbon atoms, and may be bonded to one another to form a ring structure, and p represents an integer of 0 to 6; in formula (6), R$^{16}$ to R$^{18}$ independently represent a hydrogen atom, an alkyl group having 1 to 18 carbon atoms or an aryl group having 6 to 14 carbon atoms, and may be bonded to one another to form a ring structure, R' represents a group represented by general formula (7), and q represents an integer of 0 to 3; in formula (7), R$^{19}$ to R$^{24}$ independently represent a hydrogen atom, an alkyl group having 1 to 18 carbon atoms or an aryl group having 6 to 14 carbon atoms, and may be bonded to one another to form a ring structure; in formula (8), R$^{25}$ to R$^{27}$ independently represent a hydrogen atom, an alkyl group having 1 to 18 carbon atoms or an aryl group having 6 to 14 carbon atoms, and may be bonded to one another to form a ring structure; and E represents a hydrogen atom, an alkyl group having 1 to 18 carbon atoms, an alkenyl group having 2 to 18 carbon atoms, an alkynyl group having 2 to 18 carbon atoms or a group represented by general formula (9) below, R$^{28}$ to R$^{32}$ independently represent an alkyl group having 1 to 18 carbon atoms, a nitro group, a hydroxyl group, a cyano group, an alkoxy group represented by —OR$^{39}$, an acyl group represented by R$^{40}$CO—, an acyloxy group represented by R$^{41}$COO—, an alkylthio group represented by —SR$^{42}$, an amino group represented by —NR$^{43}$R$^{44}$ or a halogen atom, R$^{28}$ to R$^{32}$ may be the same as or different from one another and may be bonded to one another to form a ring structure, in general formula (9), (G) represents a divalent group represented by general formula (10) or general formula (11), and R$^{33}$ to R$^{36}$ independently represent a hydrogen atom, an alkyl group having 1 to 18 carbon atoms or an aryl group having 6 to 14 carbon atoms, and may be the same as or different from one another.]

The ammonio group (Y$^+$) leaves in the form of a corresponding amine (Y) with photoirradiation, and functions as various reaction catalysts. On the other hand, since the ammonio group (Y$^+$) has no basicity before photoirradiation, the storage stability of a reactive composition is lowered even when the group is contained in the reactive composition.

The ammonio group (Y$^+$) is represented by any of general formulas (4) to (6) and (8) below.

[Chemical Formula 6]

(4)

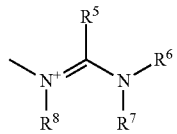

[Chemical Formula 7]

(5)

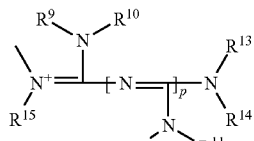

[Chemical Formula 8]

(6)

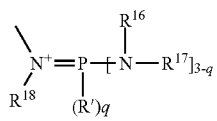

[Chemical Formula 9]

(7)

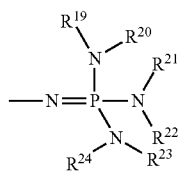

[Chemical Formula 10]

(8)

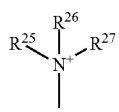

Among R$^5$ to R$^8$ in general formula (4), the alkyl group having 1 to 18 carbon atoms is the same as the above-mentioned alkyl group, the alkenyl group having 2 to 18 carbon atoms is the same as the above-mentioned alkenyl group, and the aryl group having 6 to 14 carbon atoms is the same as the above-mentioned aryl group. Moreover, these substituents may be bonded to one another to form a ring structure.

Among R$^9$ to R$^{15}$ in general formula (5), the alkyl group having 1 to 18 carbon atoms is the same as the above-mentioned alkyl group, the alkenyl group having 2 to 18 carbon atoms is the same as the above-mentioned alkenyl group, and the aryl group having 6 to 14 carbon atoms is the same as the above-mentioned aryl group. Moreover, these substituents may be bonded to one another to form a ring structure. p represents an integer of 0 to 6.

Among R$^{16}$ to R$^{18}$ in general formula (6), the alkyl group having 1 to 18 carbon atoms is the same as the above-mentioned alkyl group, and the aryl group having 6 to 14 carbon atoms is the same as the above-mentioned aryl group. Moreover, these substituents may be bonded to one another to form a ring structure.

In formula (6), R' represents a group represented by general formula (7) above. q represents an integer of 0 to 3.

In formula (7), among R$^{19}$ to R$^{24}$, the alkyl group having 1 to 18 carbon atoms is the same as the above-mentioned alkyl group, and the aryl group having 6 to 14 carbon atoms is the same as the above-mentioned aryl group. Moreover, these substituents may be bonded to one another to form a ring structure.

Among $R^{25}$ to $R^{27}$ in general formula (8), the alkyl group having 1 to 18 carbon atoms is the same as the above-mentioned alkyl group, and the aryl group having 6 to 14 carbon atoms is the same as the above-mentioned aryl group. Moreover, these substituents may be bonded to one another to form a ring structure.

E represents a hydrogen atom, an alkyl group having 1 to 18 carbon atoms, an alkenyl group having 2 to 18 carbon atoms, an alkynyl group having 2 to 18 carbon atoms or a group represented by general formula (9) below.

The alkyl group having 1 to 18 carbon atoms is the same as the above-mentioned alkyl group, the alkenyl group having 2 to 18 carbon atoms is the same as the above-mentioned alkenyl group, and the alkynyl group having 2 to 18 carbon atoms is the same as the above-mentioned alkynyl group.

[Chemical Formula 11]

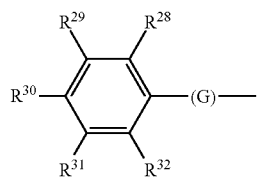

(9)

In formula (9), $R^{28}$ to $R^{32}$ independently represent an alkyl group having 1 to 18 carbon atoms, a nitro group, a hydroxyl group, a cyano group, an alkoxy group represented by —$OR^{39}$, an acyl group represented by $R^{40}CO$—, an acyloxy group represented by $R^{41}COO$—, an alkylthio group represented by —$SR^{42}$, an amino group represented by —$NR^{43}R^{44}$ or a halogen atom, and $R^{28}$ to $R^{32}$ may be the same as or different from one another and may be bonded to one another to form a ring structure.

The alkyl group having 1 to 18 carbon atoms, the alkoxy group represented by —$OR^{39}$, the acyl group represented by $R^{40}CO$—, the acyloxy group represented by $R^{41}COO$—, the alkylthio group represented by —$SR^{42}$, and the amino group represented by —$NR^{43}R^{44}$ are the same as those mentioned above.

In formula (9), (G) represents a divalent group represented by general formula (10) or general formula (11), and $R^{33}$ to $R^{36}$ independently represent a hydrogen atom, an alkyl group having 1 to 18 carbon atoms or an aryl group having 6 to 14 carbon atoms and may be the same as or different from one another.

[Chemical Formula 12]

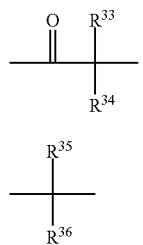

(10)

(11)

$R^{33}$ to $R^{36}$ in general formula (10) or general formula (11) independently represent a hydrogen atom, an alkyl group having 1 to 18 carbon atoms or an aryl group having 6 to 14 carbon atoms, and may be the same as or different from one another. The alkyl group having 1 to 18 carbon atoms and the aryl group having 6 to 14 carbon atoms are the same as the above-mentioned alkyl group having 1 to 18 carbon atoms and the above-mentioned aryl group having 6 to 14 carbon atoms, respectively.

Among the examples of E, preferred are a hydrogen atom, an alkyl group having 1 to 8 carbon atoms, an alkenyl group having 2 to 8 carbon atoms, a non-substituted group represented by general formula (9), and a group which is represented by general formula (9) and substituted by an alkyl group having 1 to 8 carbon atoms, a nitro group, an alkoxy group represented by —$OR^{39}$, an acyl group represented by $R^{40}CO$—, an acyloxy group represented by $R^{41}COO$—, an alkylthio group represented by —$SR^{42}$, or a halogen atom, and further preferred are a non-substituted group represented by general formula (9), and a group which is represented by general formula (9) and substituted by an alkyl group having 1 to 8 carbon atoms, a nitro group, an alkoxy group represented by —$OR^{39}$, an acyl group represented by $R^{40}CO$—, an alkylthio group represented by —$SR^{42}$, or a halogen atom.

Among the examples of E, preferred specific examples thereof include methyl, ethyl, n-butyl, isopropyl, tert-butyl, allyl, 2-butenyl, benzyl, p-nitrobenzyl, o-nitrobenzyl, 2,6-dinitrobenzyl, p-methoxybenzyl, p-butoxybenzyl, p-fluorobenzyl, p-chlorobenzyl, 4-benzoylbenzyl, 4-phenylthiobenzyl, phenacyl, 3,4-dimethoxyphenacyl, p-chlorophenacyl, p-bromophenacyl and the like.

Examples of the ammonio group ($Y^+$) in general formula (3) include ammonio groups constituted from groups in which the cation is stabilizable by virtue of the resonance structure such as amidine, guanidine and phosphazene and selected from the group of general formulas (12) to (18) below, ammonio groups constituted from general tertiary amines such as tributylamine, trioctylamine, octyldimethylamine and diisopropylethylamine, and ammonio groups selected from the group of general formulas (19) to (21) below.

Among these, preferred are ammonio groups selected from the group of general formulas (12) to (18).

[Chemical Formula 13]

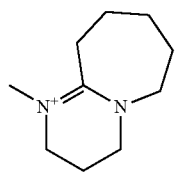

(12)

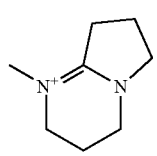

(13)

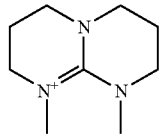

(14)

-continued

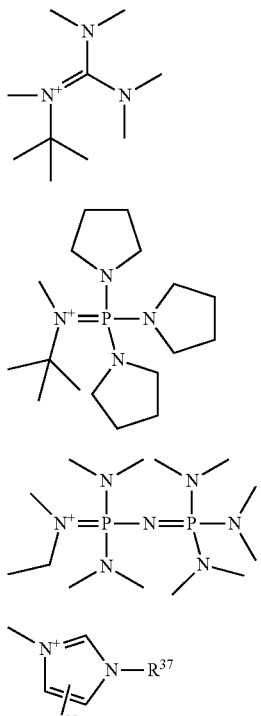

(15)

(16)

(17)

[Chemical Formula 14]

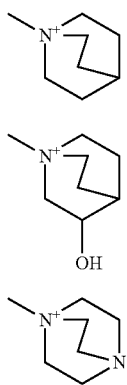

(18)

(19)

(20)

(21)

In formula (18), $R^{37}$ represents an alkyl group having 1 to 18 carbon atoms, an alkenyl group having 2 to 18 carbon atoms or an aryl group having 6 to 14 carbon atoms, $R^{38}$ represents an alkyl group having 1 to 18 carbon atoms, and $R^{37}$ and $R^{38}$ may be bonded to each other to form a ring structure. Examples of the alkyl group having 1 to 18 carbon atoms include those that are the same as the alkyl groups mentioned above.

Examples of the alkenyl group having 2 to 18 carbon atoms include the above-mentioned alkenyl groups.

Examples of the aryl group having 6 to 14 carbon atoms include the above-mentioned aryl groups.

Among these ammonio groups ($Y^+$s), preferred are (a group represented by chemical formula (12)) and (a group represented by chemical formula (13)) which are cations having an amidine skeleton; (a group represented by chemical formula (14)) and (a group represented by chemical formula (15)) which are cations having a guanidine skeleton; (a group represented by chemical formula (16)) and (a group represented by chemical formula (17)) which are cations having a phosphazene skeleton; 1-methylimidazol-3-yl, 1,2-dimethylimidazol-3-yl, 1-methyl-2-ethylimidazol-3-yl, trioctylammonio, diisopropyl ethylammonio, and (a group represented by chemical formula (19)), (a group represented by chemical formula (20)) and (a group represented by chemical formula (21)) which have a cyclic ammonio skeleton, and further preferred are (a group represented by chemical formula (12)) and (a group represented by chemical formula (13)) which are cations having an amidine skeleton; (a group represented by chemical formula (14)) and (a group represented by chemical formula (15)) which are cations having a guanidine skeleton; (a group represented by chemical formula (16)) and (a group represented by chemical formula (17)) which are cations having a phosphazene skeleton; 1-methylimidazol-3-yl, and 1,2-dimethylimidazol-3-yl.

Since the photobase generator according to the present invention has more enhanced sensitivity to light as compared with conventional photobase generators, sufficient effects are attained even when the photobase generator is used alone, but the photobase generator may be used in combination with a photosensitizer.

As the photosensitizer, known (JP-A-11-279212, JP-A-09-183960 and the like) sensitizers can be used, and examples thereof include benzoquinones {1,4-benzoquinone, 1,2-benzoquinone and the like}; naphthoquinones {1,4-naphthoquinone, 1,2-naphthoquinone and the like}; anthraquinones {2-methyl anthraquinone, 2-ethyl anthraquinone and the like}; anthracenes {anthracene, 9,10-dibutoxyanthracene, 9,10-dimethoxyanthracene, 9,10-diethoxyanthracene, 2-ethyl-9,10-dimethoxyanthracene, 9,10-dipropoxyanthracene and the like}; pyrene; 1,2-benzanthracene; perylene; tetracene; coronene; thioxanthones {thioxanthone, 2-methylthioxanthone, 2-ethylthioxanthone, 2-chlorothioxanthone, 2-isopropylthioxanthone, 2,4-diethylthioxanthone and the like}; phenothiazines {phenothiazine, N-methylphenothiazine, N-ethylphenothiazine, N-phenylphenothiazine and the like}; xanthone; naphthalenes {1-naphthol, 2-naphthol, 1-methoxynaphthalene, 2-methoxynaphthalene, 1,4-dihydroxynaphthalene, 4-methoxy-1-naphthol and the like}; ketones {dimethoxyacetophenone, diethoxyacetophenone, 2-hydroxy-2-methyl-1-phenylpropan-1-one, 4'-isopropyl-2-hydroxy-2-methyl-propiophenone, 4-benzoyl-4'-methyldiphenylsulfide and the like}; carbazole {N-phenylcarbazole, N-ethylcarbazole, poly-N-vinylcarbazole, N-glycidylcarbazole and the like}; chrysenes {1,4-dimethoxychrysene, 1,4-di-α-methylbenzyloxychrysene and the like}; phenanthrenes {9-hydroxyphenanthrene, 9-methoxyphenanthrene, 9-hydroxy-10-methoxyphenanthrene, 9-hydroxy-10-ethoxyphenanthrene and the like} and the like.

In particular, from the viewpoint of electron acceptability, a naphthoquinone-based, benzophenone-based, xanthone-based, anthraquinone-based or thioxanthone-based sensitizer is preferred because a high sensitizing effect is attained when the sensitizer is used.

The photobase generator according to the present invention can be produced by a known method. An example thereof is shown by the following chemical reaction formulas. By allowing a compound (H) having a substituent (E) corresponding to an aimed photobase generator and a leaving group (Z) as a substituent and an amine (Y) corresponding to the ammonio group ($Y^+$) to undergo a reaction directly or in a solvent, a cation intermediate containing $Z^-$ as a counter anion is obtained. This cation intermediate and a borate metal salt which has a substituent corresponding to the aimed photobase generator and is separately produced by a known method can be subjected to an anion exchange in an organic solvent or water to obtain the aimed photobase generator.

[Chemical Formula 15]

$$E-Z + Y \longrightarrow E-Y^+ \ Z^-$$

$$E-Y^+ \ Z^- + M^+ \ R^1-\underset{R^4}{\overset{R^2}{\underset{|}{B^-}}}-R^3 \longrightarrow E-Y^+ \ R^1-\underset{R^4}{\overset{R^2}{\underset{|}{B^-}}}-R^3$$

[In the formulas, E and Y+ are the same as those in general formula (1), Z is a leaving group, Z− is a counter anion generated through elimination, Y is an amine corresponding to ammonium, and M+ is a metal cation.]

Examples of the amine (Y) include a compound represented by chemical formula (22) {1,8-diazabicyclo[5.4.0]undec-7-ene (DBU; "DBU" is a registered trademark of San-Apro Ltd.)}, a compound represented by chemical formula (23) {1,5-diazabicyclo[4.3.0]non-5-ene (DBN)}, a compound represented by chemical formula (24) {7-methyl-1,5,7-triazabicyclo[4.4.0]dec-5-ene}, a compound represented by chemical formula (25) {2-tert-butyl-1,1,3,3-tetramethylguanidine}, a compound represented by chemical formula (26) {tert-butylimino-tri(pyrrolidino)phosphorane}, a compound represented by chemical formula (27) [N-(ethylimide)-N',N"-tetramethyl-N"'-{tris(dimethylamino)phosphoranylidene}phosphoric acid triamide], a compound represented by chemical formula (28) [each sign is the same as that of chemical formula (8), for example, cyclic amines such as 1-azabicyclo[2.2.2]octane {chemical formula (30)}, 3-hydroxy-1-azabicyclo[2.2.2]octane {chemical formula (31)} and 1,4-diazabicyclo[2.2.2]octane {chemical formula (32)}, chain amines such as trialkylamines (tributylamine, trioctylamine, octyldimethylamine, diisopropylethylamine and the like), trialkenylamines (triallylamine and the like) and triarylamines (triphenylamine, tri p-tolylamine, diphenyl p-tolylamine and the like) and the like], and a compound represented by chemical formula (29) (each sign is the same as that of chemical formula (18), for example, 1-methylimidazole, 1,2-dimethylimidazole, 1-methyl 2-ethylimidazole and the like}.

[Chemical Formula 16]

(22)

(23)

(24)

(25)

(26)

(27)

(28)

(29)

(30)

(31)

(32)

Examples of the leaving group (Z) include halogen atoms (a chlorine atom, a bromine atom and the like), sulfonyloxy groups (trifluoromethylsulfonyloxy, 4-methylphenylsulfonyloxy, methylsulfonyloxy and the like) and acyloxy (acetoxy, trifluoromethylcarbonyloxy and the like). Among these, from the viewpoint of production easiness, a halogen atom and a sulfonyloxy group are preferred.

As the solvent, water or an organic solvent can be used. Examples of the organic solvent include hydrocarbons (hexane, heptane, toluene, xylene and the like), cyclic ethers (tetrahydrofuran, dioxane and the like), chlorine-based solvents (chloroform, dichloromethane and the like), alcohols (methanol, ethanol, isopropyl alcohol and the like), ketones (acetone, methyl ethyl ketone, methyl isobutyl ketone and the like), nitriles (acetonitrile and the like), and polar organic solvents (dimethyl sulfoxide, dimethylformamide, N-methylpyrrolidone and the like). These solvents may be used alone and two or more kinds thereof may be used in combination.

The reaction temperature (° C.) between the compound (H) as a raw material of the cation intermediate and the amine (Y) is preferably −10° C. to 100° C., and further preferably 0° C. to 80° C. It is preferred that the compound (G) be previously dissolved in the organic solvent and then the amine be added thereto. With regard to the procedure for adding the amine, the amine may be added dropwise, and may be added dropwise after being diluted with an organic solvent.

The above-mentioned compound (H) can be produced by a known method. Among the compounds (H), when a carbon atom at the α-position having an aromatic ring group as a substituent is halogenated (preferably, brominated), a method in which halogen (preferably, bromine) is used or a method in which N-bromosuccinimide is used together with a radical generator is simple and convenient and therefore is preferable (The Fourth Series of Experimental Chemistry, Vol. 19, edited by the Chemical Society of Japan, p. 422).

The borate metal salt as an anion component is obtained by allowing an alkyl or aryl organic metal compound, and an alkyl or aryl boron compound or a halogenated boron compound to undergo a reaction in an organic solvent by means of a known method (for example, Journal of Polymer Science: Part A: Polymer Chemistry, Vol. 34, 2817 (1996), or the like serves as a useful reference). As the organic metal compound to be used, lithium compounds such as an alkyl lithium and an aryl lithium, and magnesium compounds (Grignard reagents) such as an alkyl magnesium halide and an aryl magnesium halide are suitably used.

The temperature in a reaction between the boron compound and the organic metal compound is −80° C. to 100° C., preferably −50° C. to 50° C., and most preferably −30° C. to 30° C. As the organic solvent to be used, hydrocarbons (hexane, heptane, toluene, xylene and the like), cyclic ethers (tetrahydrofuran, dioxane and the like), and chlorine-based solvents (chloroform, dichloromethane and the like) are suitably used.

From the viewpoints of stability and solubility, it is preferred that the borate metal salt obtained as above be an alkali metal salt. In the case of allowing those to undergo a reaction with a Grignard reagent, it is preferred that sodium hydrogen carbonate, sodium chloride, potassium chloride, lithium chloride, sodium bromide, potassium bromide, lithium bromide and the like be added to perform the exchange of the metal during the reaction or after the reaction.

The anion exchange is performed by mixing the borate metal salt obtained as above and an organic solvent containing an intermediate or an aqueous solution thereof.

After obtaining an intermediate, anion exchange may be performed subsequently or, alternatively, anion exchange may be performed after isolating and purifying the intermediate and then dissolving it in an organic solvent again.

The photobase generator obtained as described above may be purified after being separate from the organic solvent. The separation from the organic solvent can be performed by adding a poor solvent to an organic solvent solution containing the photobase generator directly (or after the condensation thereof) to deposit the photobase generator. Examples of the poor solvent to be used include chain ethers (diethyl ether, dipropyl ether and the like), esters (ethyl acetate, butyl acetate and the like), aliphatic hydrocarbons (hexane, cyclohexane and the like) and aromatic hydrocarbons (toluene, xylene and the like).

When the photobase generator is an oily substance, the photobase generator according to the present invention can be obtained by separating the deposited oily substance from the organic solvent solution, and furthermore, distilling away the organic solvent contained in the oily substance. On the other hand, when the photobase generator is a solid, the photobase generator according to the present invention can be obtained by separating a deposited solid from the organic solvent solution, and furthermore, distilling away the organic solvent contained in the solid.

With regard to the purification, the photobase generator can be purified by recrystallization (a method of utilizing the solubility difference caused by cooling, a method of adding a poor solvent to deposit the photobase generator, and combined use of these methods). Moreover, when the photobase generator is an oily substance (when the photobase generator is not crystallized), the photobase generator can be purified by a method of washing the oily substance with water or a poor solvent.

The photobase generator according to the present invention can be applied as a latent base catalyst (a catalyst that has no catalysis before photoirradiation but develops an action of a base catalyst through photoirradiation) and the like, can be used as a curing catalyst for a basic reactive compound, for example, a photosensitive resin composition such as a photocurable resin composition, and is suitable as a curing catalyst for a photocurable resin composition which is cured when irradiated with light. For example, a photocurable resin composition containing a basic resin in which curing is promoted by a base, the photobase generator according to the present invention, and if necessary, a solvent and/or additive can be easily constituted. Since such a photocurable resin composition contains the photobase generator according to the present invention, the photocurable resin composition is excellent in curing properties as well as excellent in preservation stability. That is, it is possible to obtain a cured material by irradiating a photocurable resin composition containing the photobase generator according to the present invention with light to generate a base and promoting a curing reaction. Thus, a production method of such a cured material preferably includes a step of irradiating the photobase generator according to the present invention with light to generate a base. In the curing reaction, heating may be performed, if necessary.

The photosensitive resin composition in which curing is promoted by a base generated by photoirradiation is not particularly limited as long as the photosensitive resin composition is a photocurable resin cured by a base, and examples thereof include curable urethane resins {resins containing a (poly)isocyanate and a curing agent (a polyol, a thiol and the like) and the like}, curable epoxy resins {resins containing a (poly)epoxide and a curing agent (an acid anhydride, a carboxylic acid, a (poly)epoxide, a thiol and the like), resins containing epichlorohydrin and a carboxylic acid, and the like}, curable acrylic resins {an acrylic monomer and/or an acrylic oligomer and a curing agent (a thiol, a malonic ester, acetylacetonato and the like)}, polysiloxane (which is cured to form a crosslinked polysiloxane), polyimide resins, and resins described in Patent Document 3.

For the photobase generator according to the present invention, there can be used an LED ultraviolet ray irradiation device, an irradiation device of laser light such as electron beam rays, an excimer laser and an Ar laser and the like, depending on the application, as well as a commonly used high pressure mercury lamp, an ultra-high pressure mercury lamp, a metal halide lamp, a high power metal halide lamp and the like (for example, see Recent Advances in UV/EB Radiation Curing Technology, edited by RadTech Japan, published by CMC Publishing CO., LTD., p. 138, 2006).

EXAMPLES

Hereinafter, the present invention will be further described by reference to examples, but the present invention is not intended to be limited thereto. It should be noted that % means % by weight unless otherwise stated.

Production Example 1 Synthesis of thioxanthone-3-carboxylic acid (Intermediate a)

(1) Synthesis of 2-(phenylthio)-dimethyl terephthalate (Intermediate a-1)

In a reaction vessel, the inside of which was replaced with nitrogen, 43 g of dimethyl 2-nitroterephthalate (available from Tokyo Chemical Industry Co., Ltd.) and 100 mL of DMF were placed, and cooled to −10° C. with an ice-salt bath. To this, separately, a sodium thiophenolate solution prepared with 22 g of thiophenol, 8 g of sodium hydride and 60 mL of DMF was added dropwise over a period of 1 hour. The contents were stirred for 3 hours at room temperature, and then, charged into water. After being extracted with ethyl acetate and removed from the aqueous layer, water washing was performed three times and the organic layer was concentrated. The concentrated organic layer was treated with hexane to obtain 45 g of a white solid. It was confirmed by $^1$H-NMR that this white solid was (Intermediate a-1).

(2) Synthesis of 2-(phenylthio)-terephthalic acid (Intermediate a-2)

In a reaction vessel equipped with a condenser, 50 g of (Intermediate a-1) and 600 mL of methanol were placed and stirred. To this, 52 g of potassium hydroxide was gradually added. The contents were refluxed for 3 hours and then concentrated. To the resultant white solid, 600 g of water was added, and the solid was heated to 70° C. and dissolved. To this, 150 g of 4N hydrochloric acid was gradually added, whereupon a solid precipitated. Filtration and drying were performed to obtain 40 g of a white solid. It was confirmed by 1H-NMR that this white solid was (Intermediate a-2).

(3) Synthesis of thioxanthone-3-carboxylic acid (Intermediate a)

In a reaction vessel, 27 g of (Intermediate a-2) and 300 g of polyphosphoric acid were placed and stirred for 18 hours at 160° C. The reaction liquid was charged in small portions into 3 L of water under stirring to precipitate a solid. The obtained solid was recrystallized from DMF/water to obtain 20 g of a yellow solid. It was confirmed by: $^1$H-NMR that this yellow solid was (Intermediate a).

Production Example 2 Synthesis of 2-mercaptothioxanthone (Intermediate b)

In a reaction vessel, 300 mL of concentrated sulfuric acid was placed, and to this, 16 g of dithiosalicylic acid (available from Wako Pure Chemical Industries, Ltd.) was added in small portions. The contents were stirred for 30 minutes, and cooled to 5° C. with an ice bath. To this, 120 g of thiophenol was added dropwise. After being stirred for 1 hour at room temperature, the contents were allowed to undergo a reaction for 5 hours at 80° C., and then, again cooled to room temperature. To 5 L of water at 80° C., the reaction liquid was added in small portions under stirring. After being cooled to room temperature, a solid precipitated was filtered. The solid was recrystallized from dioxane/water to obtain 22 g of a yellow solid. It was confirmed by 1H-NMR that this solid was (Intermediate b).

Production Example 3 Synthesis of 2-bromomethylthioxanthone (Intermediate c)

(1) 2-Methylthioxanthone (Intermediate c-1)

In a reaction vessel, 70 mL of concentrated sulfuric acid was placed, and to this, 10 g of dithiosalicylic acid (available from Wako Pure Chemical Industries, Ltd.) was added and stirred at room temperature for 1 hour. The contents were cooled with an ice bath and 25 g of toluene was added dropwise while keeping the temperature thereof at 20° C. or lower. After dropping, the temperature thereof was returned to room temperature, and furthermore, stirring was performed for 2 hours. This reaction liquid was poured into 800 g of ice water. A yellow solid precipitated was filtered off and dissolved in 200 g of dichloromethane, after which water washing was performed. The organic layer was concentrated to obtain 9 g of a yellow solid. It was confirmed by: $^1$H-NMR that this yellow solid was Intermediate (c-1).

(2) Synthesis of 2-bromomethylthioxanthone (Intermediate c)

In a reaction vessel equipped with a reflux tube, 2 g of Intermediate (c-1) was dissolved in 100 mL of cyclohexane, and to this, 8 g of N-bromosuccinimide (available from Wako Pure Chemical Industries, Ltd.) and 0.1 g of benzoyl peroxide were added. The contents were allowed to undergo a reaction for 4 hours under reflux. The solvent was distilled off, and to this, 50 mL of chloroform was added to dissolve the residue, after which water washing was performed three times. The organic layer was concentrated to obtain 2 g of a brown solid. The brown solid was recrystallized from ethyl acetate to obtain 1.8 g of a yellow solid. It was confirmed by $^1$H-NMR that this yellow solid was Intermediate (c).

Production Example 4 Synthesis of potassium (4-hydroxyethyloxy)phenyltriphenylborate (Intermediate d)

(1) Synthesis of 4-(trimethylsiloxyethyloxy)bromobenzene (Intermediate d-1)

In a reaction vessel, the inside of which was replaced with nitrogen, 15 g of 4-bromophenoxy ethanol (available from Tokyo Chemical Industry Co., Ltd.), 200 mL of THF and 8 g of triethylamine were placed. While the contents were cooled with an ice bath, 8.5 g of trimethylsilyl chloride (available from Tokyo Chemical Industry Co., Ltd.) was added dropwise. After the completion of dropping, the contents were allowed to undergo a reaction for 2 hours at room temperature, and the reaction liquid was charged into 300 mL of water. The liquid was extracted with 50 g of ethyl acetate three times and the organic layer was washed with 20 mL of water two times, after which the organic layer was concentrated to obtain 19 g of a pale brown liquid. This liquid was purified by silica gel column chromatography to obtain a colorless liquid. It was confirmed by $^1$H-NMR that this liquid was (Intermediate d-1).

(2) Synthesis of potassium (4-trimethylsiloxyethyloxy)phenyltriphenylborate (Intermediate d-2)

In a four-necked reaction vessel, the inside of which was replaced with nitrogen, 100 mL of a 0.25 molL$^{-1}$ tetrahydrofuran solution of triphenylborane (available from Aldrich) was placed, and cooled to −20° C. To this, 26 mL of a 1.0 molL$^{-1}$ Grignard reagent prepared by a routine procedure from (Intermediate d-1) was gradually added dropwise. After dropping, the contents were stirred for 2 hours at room temperature, after which to this solution, 100 ml of a saturated aqueous potassium bicarbonate solution was added, the organic layer was separated and subjected to solvent removal, and the residue was washed with hexane two times and then dried under reduced pressure to obtain a white solid.

(3) Synthesis of potassium (4-hydroxyethyloxy)phenyltriphenylborate (Intermediate d)

To Intermediate (d-2) obtained in (2), 100 mL of tetrahydrofuran was added, and to this, an aqueous potassium fluoride solution was gradually added. After being stirred overnight, 100 mL of a saturated aqueous potassium bicarbonate solution was added, and furthermore, the liquid was extracted with 100 mL of diethyl ether three times. The organic layer was concentrated to obtain 7 g of a white solid. It was confirmed by 1H-NMR that this white solid was (Intermediate d).

Production Example 5 Synthesis of potassium (4-hydroxyethyl)phenyltriphenylborate (Intermediate e)

According to the method described in Production Example 4, Intermediate e, which is an aimed product, was obtained in the same manner except that the starting material was changed.

Production Example 6 Potassium styryltriphenylborate (Synthesis of Intermediate f)

In the production of Intermediate d-2 in Production Example 4, in place of the Grignard reagent prepared from Intermediate d-1, 26 mL of a 1.0 molL$^{-1}$ Grignard reagent prepared by a routine procedure from 4-bromostyrene was used, and an aimed product was obtained according to the method described in Production Example 4 (2).

Production Example 7 Potassium 3-butenyl-triphenylborate (Synthesis of Intermediate g)

In the production of Intermediate d-2 in Production Example 4, in place of the Grignard reagent prepared from Intermediate d-1, 26 mL of a 1.0 molL$^{-1}$ Grignard reagent prepared by a routine procedure from 4-bromo-1-butene was used, and an aimed product was obtained according to the method described in Production Example 4 (2).

Production Example 8 Synthesis of potassium (4-hydroxyethyloxy)phenyltrinaphthylborate (Intermediate h)

In the synthesis of Intermediate d-2 in Production Example 4, in place of the 0.25 molL$^{-1}$ tetrahydrofuran solution of triphenylborane (available from Aldrich), a 0.25 molL$^{-1}$ trinaphthylborane solution was prepared in the following way.

In a reaction vessel, the inside of which was replaced with nitrogen, 7.1 g of a boron trifluoride-ether complex and 100 mL of THF were placed, and cooled to 0° C. To this, 100 mL of a 0.5 molL$^{-1}$ THF solution of 2-naphthylmagnesium bromide (available from Aldrich) was added dropwise. After dropping, the contents were allowed to undergo a reaction for 6 hours at room temperature, and added with 100 mL of hexane to perform filtration. The organic layer was concentrated to obtain a white solid. This solid was added with 200 mL of THF to prepare a 0.25 molL$^{-1}$ tetrahydrofuran solution of trinaphthylborane.

Thus, an aimed product was obtained according to the method described in Production Example 4 except that the 0.25 molL$^{-1}$ tetrahydrofuran solution of trinaphthylborane was used.

Production Example 9 Synthesis of 2-mercaptomethylthioxanthone (Intermediate i)

In 150 mL of DMF, 15 g of (Intermediate c) obtained in Production Example 3 was dissolved, and to this, 7 g of potassium thioacetate (available from Wako Pure Chemical Industries, Ltd.) was added, and stirred for 6 hours under room temperature. The reaction liquid was charged into 500 g of water, and extracted with ethyl acetate. In 80 mL of methanol, 6 g of a yellow solid obtained by concentrating the organic layer was dissolved, and to this, 4 g of potassium carbonate was added. After being stirred for 1 hour at room temperature, 20 mL of 1N HCL was added. In 100 mL of chloroform, a solid precipitated was dissolved, and the organic layer was washed with water and then concentrated. This liquid was purified by silica gel column chromatography to obtain 5 g of a yellow solid. It was confirmed by $^1$H-NMR that this yellow solid was (Intermediate i).

Production Example 10 Synthesis of Potassium Salt A-1

In a reaction vessel, 10 g of (Intermediate d) obtained in Production Example 4 was dissolved in 50 mL of DMF, and to this, 2 g of potassium hydroxide was added and stirred. To this, a solution prepared by dissolving 8 g of (Intermediate c) obtained in Production Example 3 in 50 mL of DMF was gradually added. After being stirred for 20 hours, the reaction liquid was poured into 500 mL of water, and a yellow solid precipitated was filtered. After being dried under reduced pressure, 11 g of a yellow solid was obtained. It was confirmed by $^1$H-NMR that this yellow solid was Potassium salt A-1.

Production Example 11 Synthesis of Potassium Salt A-2

In a reaction vessel, 15 g of (Intermediate a) obtained in Production Example 1, 20 mL of dioxane and 20 mL of thionyl chloride were placed, and allowed to undergo a reaction for 6 hours under reflux. After being cooled to room temperature, the reaction liquid was concentrated, 50 mL of dichloromethane was added to the residue, and to this, a solution prepared from 20 g of (Intermediate d) obtained in Production Example 4, 0.5 g of dimethylaminopyridine (available from Tokyo Chemical Industry Co., Ltd.), 50 mL of triethylamine and 50 mL of dichloromethane was added. The contents were allowed to undergo a reaction for 20 hours under room temperature, and the reaction liquid was concentrated. To this, 100 mL of dichloromethane was added, and the liquid was washed with 1N hydrochloric acid two times, after which the organic layer was concentrated. This liquid was purified by silica gel column chromatography to obtain 10 g of a yellow solid. It was confirmed by $^1$H-NMR that this yellow solid was Potassium salt A-2.

Production Example 12 Synthesis of Potassium Salt A-3

An aimed product was obtained according to the method described in Production Example 10 except that 10 g of (Intermediate e) was used in place of 10 g of (Intermediate d) in Production Example 10. It was confirmed by $^1$H-NMR that this yellow solid was Potassium salt A-3.

Production Example 13 Synthesis of Potassium Salt A-4

An aimed product was obtained according to the method described in Production Example 11 except that 20 g of (Intermediate e) was used in place of 20 g of (Intermediate d) in Production Example 11. It was confirmed by $^1$H-NMR that this yellow solid was Potassium salt A-4.

Production Example 14 Synthesis of Potassium Salt A-5

In a reaction vessel, 3 g of (Intermediate b), 4 g of (Intermediate f) and 100 mL of cyclohexane were placed, and allowed to undergo a reaction for 24 hours under reflux with heating. This liquid was concentrated, and the obtained brown solid was purified by silica gel column chromatography to obtain a yellow solid. It was confirmed by $^1$H-NMR that this yellow solid was Potassium salt A-5.

Production Example 15 Synthesis of Potassium Salt A-6

An aimed product was obtained according to the method described in Production Example 14 except that 3 g of (Intermediate g) was used in place of 4 g of (Intermediate f) in Production Example 14. It was confirmed by $^1$H-NMR that this yellow solid was Potassium salt A-6.

Production Example 16 Synthesis of Potassium Salt A-7

An aimed product was obtained according to the method described in Production Example 10 except that 14 g of (Intermediate h) was used in place of 10 g of (Intermediate d) in Production Example 10. It was confirmed by $^1$H-NMR that this yellow solid was Potassium salt A-7.

Production Example 17 Synthesis of Potassium Salt A-8

An aimed product was obtained according to the method described in Production Example 11 except that 14 g of (Intermediate h) was used in place of 10 g of (Intermediate d) in Production Example 11. It was confirmed by $^1$H-NMR that this yellow solid was Potassium salt A-8.

Production Example 18 Synthesis of Potassium Salt A-9

An aimed product was obtained according to the method described in Production Example 11 except that 13 g of anthraquinone-2-carboxylic acid (available from Tokyo Chemical Industry Co., Ltd.) was used in place of 15 g of (Intermediate a) in Production Example 11. It was confirmed by $^1$H-NMR that this pale yellow solid was Potassium salt A-9.

Production Example 19 Synthesis of Potassium Salt A-10

An aimed product was obtained according to the method described in Production Example 11 except that 20 g of (Intermediate e) was used in place of 20 g of (Intermediate d) and 13 g of anthraquinone-2-carboxylic acid (available from Tokyo Chemical Industry Co., Ltd.) was used in place of 15 g of (Intermediate a) in Production Example 11. It was confirmed by $^1$H-NMR that this pale yellow solid was Potassium salt A-10.

Production Example 20 Synthesis of Potassium salt A-11

An aimed product was obtained according to the method described in Production Example 14 except that 3 g of (Intermediate i) was used in place of 3 g of (Intermediate b) in Production Example 14. It was confirmed by $^1$H-NMR that this yellow solid was Potassium salt A-11.

Example 1 Synthesis of Compound B-1

(1) Synthesis of Intermediate (CA-1 Chloride)

In 100 g of chloroform, 23 g of benzyl chloride was dissolved, and to this, 27 g of 1,8-diazabicyclo[5.4.0]undec-7-ene (DBU, available from San-Apro Ltd.) was added dropwise. The contents were stirred under room temperature. After 2 hours, the disappearance of the raw materials was confirmed by HPLC, and a 50% chloroform solution of an intermediate (CA-1 Chloride) was obtained.

(2) Synthesis of Compound B-1

To 10 g of the 50% chloroform solution of an intermediate (CA-1 Chloride) obtained in (1), 11 g of (Potassium salt A-1) obtained in Production Example 10 and 50 g of ion-exchanged water were added and stirred for 3 hours at room temperature. An organic layer was washed with 50 g of ion-exchanged water three times. The organic layer was concentrated and the solvent was evaporated, after which the residue was subjected to silica gel chromatography to obtain a yellow solid. It was confirmed by $^1$H-NMR that this yellow solid was Compound B-1. The structure of Compound B-1 was described in Table 1.

Example 2 Synthesis of Compound B-2

An aimed product was prepared according to the method described in Example 1 except that 12 g of (Potassium salt A-2) obtained in Production Example 11 was used in place of 11 g of (Potassium salt A-1) in Example 1. The structure of Compound B-2 was described in Table 1.

Example 3 Synthesis of Compound B-3

An aimed product was prepared according to the method described in Example 1 except that 11 g of (Potassium salt A-3) obtained in Production Example 12 was used in place of 11 g of (Potassium salt A-1) in Example 1. The structure of Compound B-3 was described in Table 1.

Example 4 Synthesis of Compound B-4

An aimed product was prepared according to the method described in Example 1 except that 11 g of (Potassium salt A-4) obtained in Production Example 13 was used in place of 11 g of (Potassium salt A-1) in Example 1. The structure of Compound B-4 was described in Table 1.

Example 5 Synthesis of Compound B-5

An aimed product was prepared according to the method described in Example 1 except that 11 g of (Potassium salt A-5) obtained in Production Example 14 was used in place of 11 g of (Potassium salt A-1) in Example 1. The structure of Compound B-5 was described in Table 1.

Example 6 Synthesis of Compound B-6

An aimed product was prepared according to the method described in Example 1 except that 10 g of (Potassium salt A-6) obtained in Production Example 15 was used in place of 11 g of (Potassium salt A-1) in Example 1. The structure of Compound B-6 was described in Table 1.

Example 7 Synthesis of Compound B-7

An aimed product was prepared according to the method described in Example 1 except that 14 g of (Potassium salt A-7) obtained in Production Example 16 was used in place of 11 g of (Potassium salt A-1) in Example 1. The structure of Compound B-7 was described in Table 1.

Example 8 Synthesis of Compound B-8

An aimed product was prepared according to the method described in Example 1 except that 14 g of (Potassium salt A-8) obtained in Production Example 17 was used in place of 11 g of (Potassium salt A-1) in Example 1. The structure of Compound B-8 was described in Table 1.

Example 9 Synthesis of Compound B-9

An aimed product was prepared according to the method described in Example 1 except that 12 g of (Potassium salt A-9) obtained in Production Example 18 was used in place of 11 g of (Potassium salt A-1) in Example 1. The structure of Compound B-9 was described in Table 1.

Example 10 Synthesis of Compound B-10

An aimed product was prepared according to the method described in Example 1 except that 11 g of (Potassium salt A-10) obtained in Production Example 19 was used in place of 11 g of (Potassium salt A-1) in Example 1. The structure of Compound B-10 was described in Table 1.

Example 11 Synthesis of Compound B-11

An aimed product was prepared according to the method described in Example 1 except that 11 g of (Potassium salt A-11) obtained in Production Example 20 was used in place of 11 g of (Potassium salt A-1) in Example 1. The structure of Compound B-11 was described in Table 1.

Example 12 to Example 22 Synthesis of Compound B-12 to Compound B-22

(1) Synthesis of Intermediate (CA-2 Chloride)

An aimed product was prepared according to the method described in Synthesis of intermediate (CA-1 Chloride) except that 14 g of 1,5-diazabicyclo[4.3.0]non-5-ene (DBN, available from San-Apro Ltd.) was used in place of 17 g of DBU in Synthesis of intermediate (CA-1 Chloride) of Example 1, and a 50% chloroform solution of an intermediate (CA-2 Chloride) was obtained.

(2) Synthesis of Compound B-12 to Compound B-22

Respective compounds were obtained by the methods described in Examples 1 to 11 respectively except that the intermediate (CA-1 Chloride) was changed to the intermediate (CA-2 Chloride) in Examples 1 to 11. It was confirmed by $^1$H-NMR that the respective compounds were aimed products. The structures of Compound B-12 to Compound B-22 were described in Table 1.

Example 23 to Example 33 Synthesis of Compound B-23 to Compound B-33

(1) Synthesis of Intermediate (CA-3 Chloride)

An aimed product was prepared according to the method described in Synthesis of intermediate (CA-1 Chloride) except that 10 g of 1-methylimidazole (available from Tokyo Chemical Industry Co., Ltd.) was used in place of 17 g of DBU in Synthesis of intermediate (CA-1 Chloride) of Example 1, and a 50% chloroform solution of an intermediate (CA-3 Chloride) was obtained.

(2) Synthesis of Compound B-23 to Compound B-33

Respective compounds were obtained by the methods described in Examples 1 to 11 respectively except that the intermediate (CA-1 Chloride) was changed to the intermediate (CA-3 Chloride) in Examples 1 to 11. It was confirmed by: $^1$H-NMR that the respective compounds were aimed products. The structures of Compound B-23 to Compound B-33 were described in Table 1.

Example 34 to Example 44 Synthesis of Compound B-34 to Compound B-44

(1) Synthesis of Intermediate (CA-4 Bromide)

An aimed product was prepared according to the method described in Synthesis of intermediate (CA-1 Chloride) except that 37 g of phenacyl bromide (available from Tokyo Chemical Industry Co., Ltd.) was used in place of 23 g of benzyl chloride in Synthesis of intermediate (CA-1 Chloride) of Example 1, and a 50% chloroform solution of an intermediate (CA-4 Bromide) was obtained.

(2) Synthesis of Compound B-34 to Compound B-44

Respective compounds were obtained by the methods described in Examples 1 to 11 respectively except that the intermediate (CA-1 Chloride) was changed to the intermediate (CA-4 Bromide) in Examples 1 to 11. It was confirmed by $^1$H-NMR that the respective compounds were aimed products. The structures of Compound B-34 to Compound B-44 were described in Table 1.

Example 45 to Example 55 Synthesis of Compound B-45 to Compound B-55

(1) Synthesis of Intermediate (CA-5 Bromide)

An aimed product was prepared according to the method described in Synthesis of intermediate (CA-4 Bromide) except that 14 g of DBN was used in place of 17 g of DBU in Synthesis of intermediate (CA-4 Bromide) of Example 31, and a 50% chloroform solution of an intermediate (CA-5 Bromide) was obtained.

(2) Synthesis of Compound B-45 to Compound B-55

Respective compounds were obtained by the methods described in Examples 1 to 11 respectively except that the intermediate (CA-1 Chloride) was changed to the intermediate (CA-5 Bromide) in Examples 1 to 11. It was confirmed by $^1$H-NMR that the respective compounds were aimed products. The structures of Compound B-45 to Compound B-55 were described in Table 1.

Example 56 to Example 66 Synthesis of Compound B-56 to Compound B-66

(1) Synthesis of Intermediate (CA-6 Bromide)

An aimed product was prepared according to the method described in Synthesis of intermediate (CA-4 Bromide) except that 10 g of 1-methylimidazole (available from Tokyo Chemical Industry Co., Ltd.) was used in place of 17 g of DBU in Synthesis of intermediate (CA-4 Bromide) of Example 31, and a 50% chloroform solution of an intermediate (CA-6 Bromide) was obtained.

(2) Synthesis of Compound B-56 to Compound B-66

Respective compounds were obtained by the methods described in Examples 1 to 11 respectively except that the intermediate (CA-1 Chloride) was changed to the intermediate (CA-6 Bromide) in Examples 1 to 11. It was confirmed by $^1$H-NMR that the respective compounds were aimed products. The structures of Compound B-56 to Compound B-66 were described in Table 1.

Example 67 to Example 77 Synthesis of Compound B-67 to Compound B-77

(1) Synthesis of Intermediate (CA-7 Chloride)

An aimed product was prepared according to the method described in Synthesis of intermediate (CA-1 Chloride) except that 17 g of 7-methyl-1,5,7-triazabicyclo[4.4.0]dec-5-ene (available from Tokyo Chemical Industry Co., Ltd.) was used in place of 17 g of DBU in Synthesis of intermediate (CA-1 Chloride) of Example 1, and a 50% chloroform solution of an intermediate (CA-7 Chloride) was obtained.

(2) Synthesis of Compound B-67 to Compound B-77

Respective compounds were obtained by the methods described in Examples 1 to 11 respectively except that the intermediate (CA-1 Chloride) was changed to the intermediate (CA-7 Chloride) in Examples 1 to 11. It was confirmed by $^1$H-NMR that the respective compounds were aimed products. The structures of Compound B-67 to Compound B-77 were described in Table 1.

Example 78 to Example 88 Synthesis of Compound B-78 to Compound B-88

(1) Synthesis of Intermediate (CA-8 Chloride)

An aimed product was prepared according to the method described in Synthesis of intermediate (CA-1 Chloride) except that 19 g of 2-tert-butyl-1,1,3,3-tetramethylguanidine (available from Aldrich) was used in place of 17 g of DBU in Synthesis of intermediate (CA-1 Chloride) of Example 1, and a 50% chloroform solution of an intermediate (CA-8 Chloride) was obtained.

(2) Synthesis of Compound B-78 to Compound B-88

Respective compounds were obtained by the methods described in Examples 1 to 11 respectively except that the intermediate (CA-1 Chloride) was changed to the intermediate (CA-8 Chloride) in Examples 1 to 11. It was confirmed by $^1$H-NMR that the respective compounds were aimed products. The structures of Compound B-78 to Compound B-88 were described in Table 1.

Example 89 to Example 99 Synthesis of Compound B-89 to Compound B-99

(1) Synthesis of Intermediate (CA-9 Chloride)

An aimed product was prepared according to the method described in Synthesis of intermediate (CA-1 Chloride) except that 35 g of tert-butylimino-tri(pyrrolidino)phosphorane (available from Aldrich) was used in place of 17 g of DBU in Synthesis of intermediate (CA-1 Chloride) of Example 1, and a 50% chloroform solution of an intermediate (CA-9 Chloride) was obtained.

(2) Synthesis of Compound B-89 to Compound B-99

Respective compounds were obtained by the methods described in Examples 1 to 11 respectively except that the intermediate (CA-1 Chloride) was changed to the intermediate (CA-9 Chloride) in Examples 1 to 11. It was confirmed by $^1$H-NMR that the respective compounds were aimed products. The structures of Compound B-89 to Compound B-99 were described in Table 1.

Example 100 to Example 110 Synthesis of Compound B-100 to Compound B-110

(1) Synthesis of Intermediate (CA-10 Chloride)

An aimed product was prepared according to the method described in Synthesis of intermediate (CA-1 Chloride) except that 35 g of N-(ethylimide)-N',N''-tetramethyl-N'''-(tris(dimethylamino)phosphoranylidene)phosphoric triamide (available from Aldrich) was used in place of 17 g of DBU in Synthesis of intermediate (CA-1 Chloride) of Example 1, and a 50% chloroform solution of an intermediate (CA-10 Chloride) was obtained.

(2) Synthesis of Compound B-100 to Compound B-110

Respective compounds were obtained by the methods described in Examples 1 to 11 respectively except that the intermediate (CA-1 Chloride) was changed to the intermediate (CA-10 Chloride) in Examples 1 to 11. It was confirmed by $^1$H-NMR that the respective compounds were aimed products. The structures of Compound B-100 to Compound B-110 were described in Table 1.

[Chemical Formula 17]

(A-1)

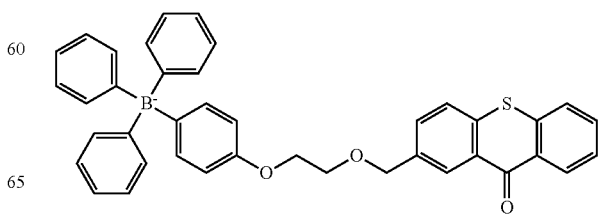

(A-2) 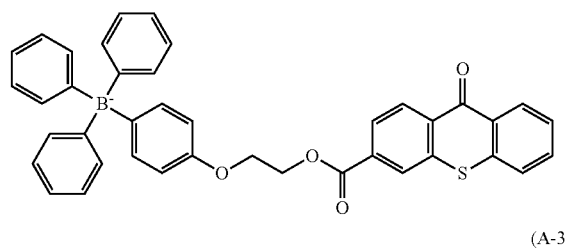
(A-3) 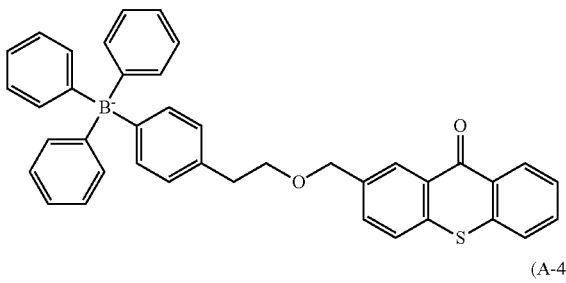
(A-4) 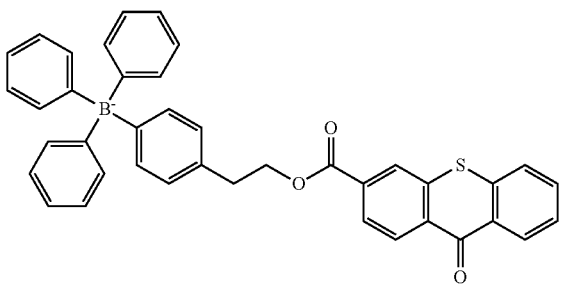
(A-5) 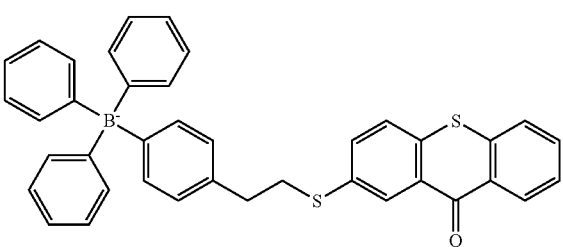
(A-6) 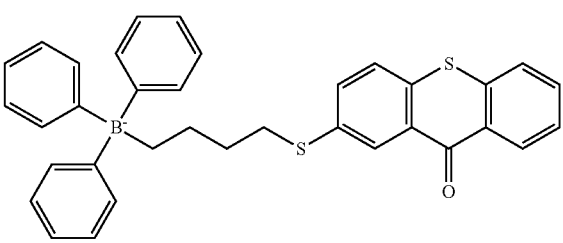
(A-7) 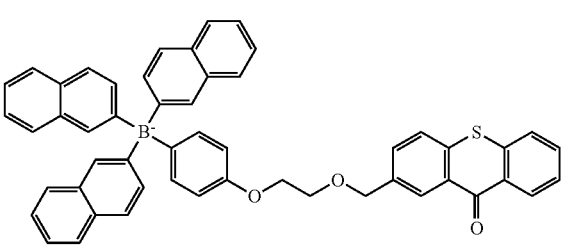
(A-8) 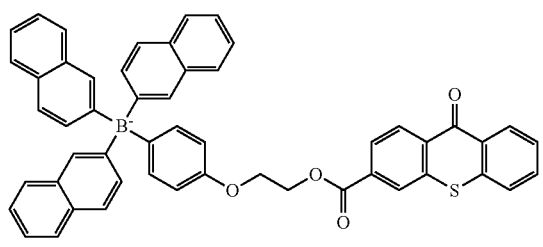
(A-9) 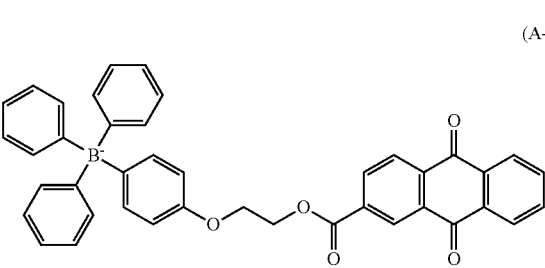
(A-10) 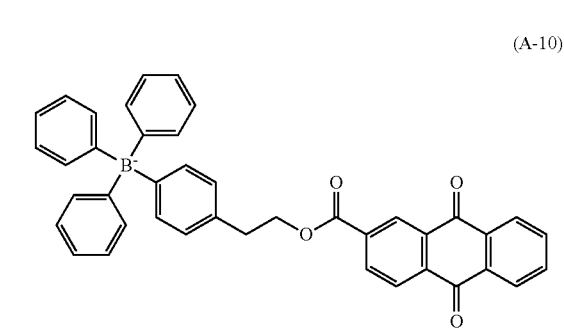
(A-11) 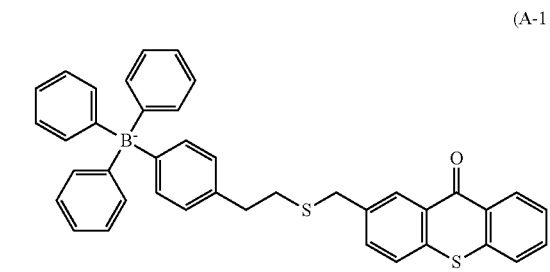
[Chemical Formula 18]
(CA-1) 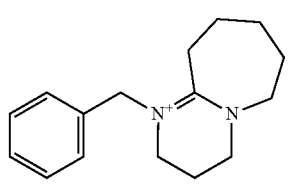
(CA-2) 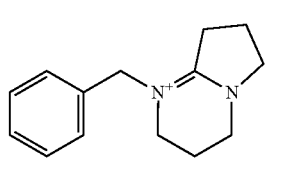
(CA-3) 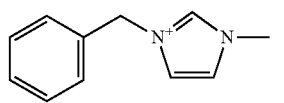

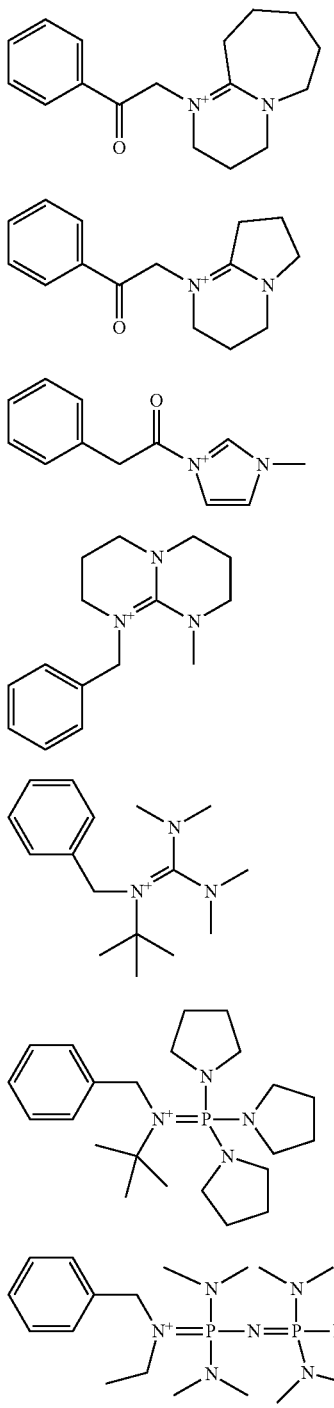

| Example | Compound | Cation | Anion |
|---|---|---|---|
| 8 | B-8 | CA-1 | A-8 |
| 9 | B-9 | CA-1 | A-9 |
| 10 | B-10 | CA-1 | A-10 |
| 11 | B-11 | CA-1 | A-11 |
| 12 | B-12 | CA-2 | A-1 |
| 13 | B-13 | CA-2 | A-2 |
| 14 | B-14 | CA-2 | A-3 |
| 15 | B-15 | CA-2 | A-4 |
| 16 | B-16 | CA-2 | A-5 |
| 17 | B-17 | CA-2 | A-6 |
| 18 | B-18 | CA-2 | A-7 |
| 19 | B-19 | CA-2 | A-8 |
| 20 | B-20 | CA-2 | A-9 |
| 21 | B-21 | CA-2 | A-10 |
| 22 | B-22 | CA-2 | A-11 |
| 23 | B-23 | CA-3 | A-1 |
| 24 | B-24 | CA-3 | A-2 |
| 25 | B-25 | CA-3 | A-3 |
| 26 | B-26 | CA-3 | A-4 |
| 27 | B-27 | CA-3 | A-5 |
| 28 | B-28 | CA-3 | A-6 |
| 29 | B-29 | CA-3 | A-7 |
| 30 | B-30 | CA-3 | A-8 |
| 31 | B-31 | CA-3 | A-9 |
| 32 | B-32 | CA-3 | A-10 |
| 33 | B-33 | CA-3 | A-11 |
| 34 | B-34 | CA-4 | A-1 |
| 35 | B-35 | CA-4 | A-2 |
| 36 | B-36 | CA-4 | A-3 |
| 37 | B-37 | CA-4 | A-4 |
| 38 | B-38 | CA-4 | A-5 |
| 39 | B-39 | CA-4 | A-6 |
| 40 | B-40 | CA-4 | A-7 |
| 41 | B-41 | CA-4 | A-8 |
| 42 | B-42 | CA-4 | A-9 |
| 43 | B-43 | CA-4 | A-10 |
| 44 | B-44 | CA-4 | A-11 |
| 45 | B-45 | CA-5 | A-1 |
| 46 | B-46 | CA-5 | A-2 |
| 47 | B-47 | CA-5 | A-3 |
| 48 | B-48 | CA-5 | A-4 |
| 49 | B-49 | CA-5 | A-5 |
| 50 | B-50 | CA-5 | A-6 |
| 51 | B-51 | CA-5 | A-7 |
| 52 | B-52 | CA-5 | A-8 |
| 53 | B-53 | CA-5 | A-9 |
| 54 | B-54 | CA-5 | A-10 |
| 55 | B-55 | CA-5 | A-11 |
| 56 | B-56 | CA-6 | A-1 |
| 57 | B-57 | CA-6 | A-2 |
| 58 | B-58 | CA-6 | A-3 |
| 59 | B-59 | CA-6 | A-4 |
| 60 | B-60 | CA-6 | A-5 |
| 61 | B-61 | CA-6 | A-6 |
| 62 | B-62 | CA-6 | A-7 |
| 63 | B-63 | CA-6 | A-8 |
| 64 | B-64 | CA-6 | A-9 |
| 65 | B-65 | CA-6 | A-10 |
| 66 | B-66 | CA-6 | A-11 |
| 67 | B-67 | CA-7 | A-1 |
| 68 | B-68 | CA-7 | A-2 |
| 69 | B-69 | CA-7 | A-3 |
| 70 | B-70 | CA-7 | A-4 |
| 71 | B-71 | CA-7 | A-5 |
| 72 | B-72 | CA-7 | A-6 |
| 73 | B-73 | CA-7 | A-7 |
| 74 | B-74 | CA-7 | A-8 |
| 75 | B-75 | CA-7 | A-9 |
| 76 | B-76 | CA-7 | A-10 |
| 77 | B-77 | CA-7 | A-11 |
| 78 | B-78 | CA-8 | A-1 |
| 79 | B-79 | CA-8 | A-2 |
| 80 | B-80 | CA-8 | A-3 |
| 81 | B-81 | CA-8 | A-4 |
| 82 | B-82 | CA-8 | A-5 |
| 83 | B-83 | CA-8 | A-6 |
| 84 | B-84 | CA-8 | A-7 |
| 85 | B-85 | CA-8 | A-8 |

TABLE 1

| Example | Compound | Cation | Anion |
|---|---|---|---|
| 1 | B-1 | CA-1 | A-1 |
| 2 | B-2 | CA-1 | A-2 |
| 3 | B-3 | CA-1 | A-3 |
| 4 | B-4 | CA-1 | A-4 |
| 5 | B-5 | CA-1 | A-5 |
| 6 | B-6 | CA-1 | A-6 |
| 7 | B-7 | CA-1 | A-7 |

TABLE 1-continued

| Example | Compound | Cation | Anion |
|---|---|---|---|
| 86 | B-86 | CA-8 | A-9 |
| 87 | B-87 | CA-8 | A-10 |
| 88 | B-88 | CA-8 | A-11 |
| 89 | B-89 | CA-9 | A-1 |
| 90 | B-90 | CA-9 | A-2 |
| 91 | B-91 | CA-9 | A-3 |
| 92 | B-92 | CA-9 | A-4 |
| 93 | B-93 | CA-9 | A-5 |
| 94 | B-94 | CA-9 | A-6 |
| 95 | B-95 | CA-9 | A-7 |
| 96 | B-96 | CA-9 | A-8 |
| 97 | B-97 | CA-9 | A-9 |
| 98 | B-98 | CA-9 | A-10 |
| 99 | B-99 | CA-9 | A-11 |
| 100 | B-100 | CA-10 | A-1 |
| 101 | B-101 | CA-10 | A-2 |
| 102 | B-102 | CA-10 | A-3 |
| 103 | B-103 | CA-10 | A-4 |
| 104 | B-104 | CA-10 | A-5 |
| 105 | B-105 | CA-10 | A-6 |
| 106 | B-106 | CA-10 | A-7 |
| 107 | B-107 | CA-10 | A-8 |
| 108 | B-108 | CA-10 | A-9 |
| 109 | B-109 | CA-10 | A-10 |
| 110 | B-110 | CA-10 | A-11 |

Comparative Example 1 Synthesis of Photobase Generator (H-1) Below

According to the method described in Patent Document 7 (WO 2009/122664 A), an aimed product was synthesized.

[Chemical Formula 19]

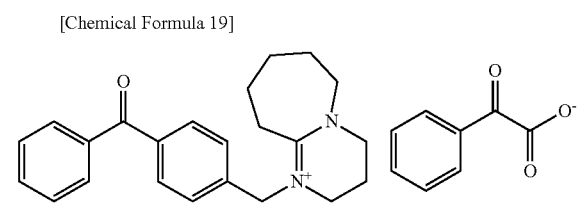

Comparative Example 2 Synthesis of Photobase Generator (H-2) Below

According to the method described in Patent Document 7 (WO 2009/122664 A), an aimed product was synthesized.

[Chemical Formula 20]

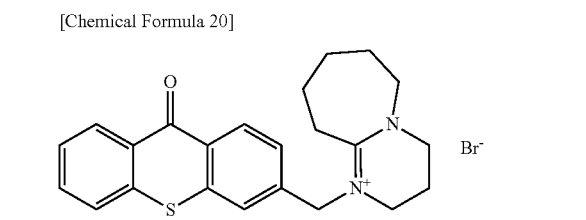

Comparative Example 3 Synthesis of Photobase Generator (H-3) Below

According to the method described in Patent Document 7 (WO 2009/122664 A), an aimed product was synthesized.

[Chemical Formula 21]

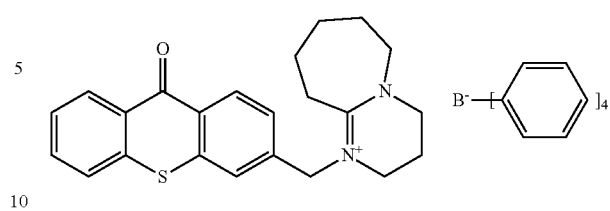

Comparative Example 4 Synthesis of Photobase Generator (H-4) Below

Based on the method described in Patent Document 7 (WO 2009/122664 A), an aimed product was synthesized.

[Chemical Formula 22]

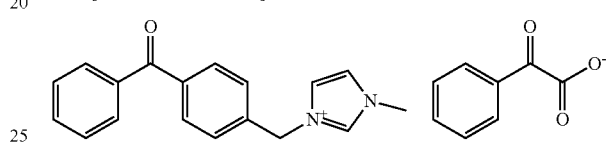

Comparative Example 5 Synthesis of Photobase Generator (H-5) Below

Based on the method described in Patent Document 7 (WO 2009/122664 A), an aimed product was synthesized.

[Chemical Formula 23]

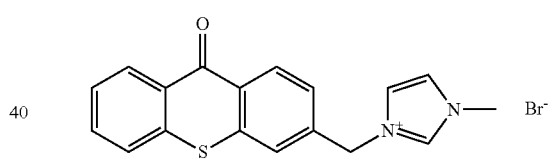

Comparative Example 6 Synthesis of Photobase Generator (H-6) Below

Based on the method described in Patent Document 7 (WO 2009/122664 A), an aimed product was synthesized.

[Chemical Formula 24]

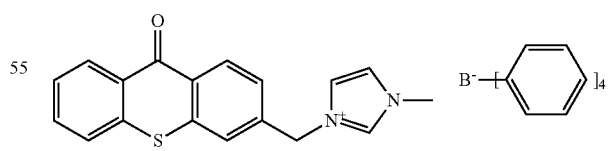

Examples 111 to 198

Comparative Examples 1 to 3

By uniformly mixing 10 g of a bisphenol A type epoxy resin (Epikote 828, available from Mitsubishi Chemical Corporation), 9 g of an acid anhydride (HN5500E, available from Hitachi Chemical Company, Ltd.) and 0.5 g of a photobase generator, a mixture was prepared. The mixture was coated on a glass substrate (76 mm×52 mm) by means of an applicator (40 μm) and then subjected to exposure with a belt conveyor type UV irradiation device (EYE GRAPHICS Co., Ltd. ECS-151U) to generate a base, immediately after which subsequently, the glass substrate was placed on a hot plate heated to 120° C. and the time required for the tackiness of the coated surface to be eliminated was measured. These results were shown in Table 2.

Examples 199 to 220, Comparative Examples 4 to 6

By uniformly mixing 10 g of a bisphenol A type epoxy resin (Epikote 828, available from Mitsubishi Chemical Corporation) and 0.5 g of a photobase generator, a curable composition was prepared.

This curable composition was coated on a glass substrate (76 mm×52 mm) by means of an applicator (40 μm) and then subjected to exposure with a belt conveyor type UV irradiation device (EYE GRAPHICS Co., Ltd. ECS-151U) to generate a base, and the gel time at 150° C. was measured in accordance with the procedure of JISK5909. These results were shown in Table 3.

TABLE 2

| Example | Compound | Tack-free time (min) |
|---------|----------|----------------------|
| 111 | B-1 | 13 |
| 112 | B-2 | 20 |
| 113 | B-3 | 10 |
| 114 | B-4 | 16 |
| 115 | B-5 | 12 |
| 116 | B-6 | 10 |
| 117 | B-7 | 13 |
| 118 | B-8 | 18 |
| 119 | B-9 | 16 |
| 120 | B-10 | 15 |
| 121 | B-11 | 10 |
| 122 | B-12 | 12 |
| 123 | B-13 | 21 |
| 124 | B-14 | 11 |
| 125 | B-15 | 15 |
| 126 | B-16 | 12 |
| 127 | B-17 | 10 |
| 128 | B-18 | 13 |
| 129 | B-19 | 18 |
| 130 | B-20 | 16 |
| 131 | B-21 | 14 |
| 132 | B-22 | 10 |
| 133 | B-34 | 15 |
| 134 | B-35 | 22 |
| 135 | B-36 | 12 |
| 136 | B-37 | 18 |
| 137 | B-38 | 14 |
| 138 | B-39 | 12 |
| 139 | B-40 | 15 |
| 140 | B-41 | 20 |
| 141 | B-42 | 18 |
| 142 | B-43 | 17 |
| 143 | B-44 | 12 |
| 144 | B-45 | 14 |
| 145 | B-46 | 24 |
| 146 | B-47 | 13 |
| 147 | B-48 | 17 |
| 148 | B-49 | 14 |
| 149 | B-50 | 13 |
| 150 | B-51 | 15 |
| 151 | B-52 | 24 |
| 152 | B-53 | 20 |
| 153 | B-54 | 18 |
| 154 | B-55 | 13 |

TABLE 2-continued

| Example | Compound | Tack-free time (min) |
|---------|----------|----------------------|
| 155 | B-67 | 15 |
| 156 | B-68 | 25 |
| 157 | B-69 | 13 |
| 158 | B-70 | 18 |
| 159 | B-71 | 15 |
| 160 | B-72 | 13 |
| 161 | B-73 | 15 |
| 162 | B-74 | 22 |
| 163 | B-75 | 19 |
| 164 | B-76 | 17 |
| 165 | B-77 | 13 |
| 166 | B-78 | 12 |
| 167 | B-79 | 19 |
| 168 | B-80 | 10 |
| 169 | B-81 | 15 |
| 170 | B-82 | 11 |
| 171 | B-83 | 9 |
| 172 | B-84 | 12 |
| 173 | B-85 | 17 |
| 174 | B-86 | 15 |
| 175 | B-87 | 14 |
| 176 | B-88 | 9 |
| 177 | B-89 | 15 |
| 178 | B-90 | 22 |
| 179 | B-91 | 12 |
| 180 | B-92 | 18 |
| 181 | B-93 | 14 |
| 182 | B-94 | 12 |
| 183 | B-95 | 15 |
| 184 | B-96 | 20 |
| 185 | B-97 | 18 |
| 186 | B-98 | 17 |
| 187 | B-99 | 12 |
| 188 | B-100 | 14 |
| 189 | B-101 | 21 |
| 190 | B-102 | 11 |
| 191 | B-103 | 17 |
| 192 | B-104 | 13 |
| 193 | B-105 | 11 |
| 194 | B-106 | 14 |
| 195 | B-107 | 19 |
| 196 | B-108 | 17 |
| 197 | B-109 | 16 |
| 198 | B-110 | 11 |
| Comparative Example 1 | H-1 | 120< |
| 2 | H-2 | Not cured |
| 3 | H-3 | 90 |

TABLE 3

| Example | Compound | Gel time (Sec) |
|---------|----------|----------------|
| 199 | B-23 | 100 |
| 200 | B-24 | 120 |
| 201 | B-25 | 90 |
| 202 | B-26 | 110 |
| 203 | B-27 | 95 |
| 204 | B-28 | 80 |
| 205 | B-29 | 105 |
| 206 | B-30 | 120 |
| 207 | B-31 | 115 |
| 208 | B-32 | 110 |
| 209 | B-33 | 80 |
| 210 | B-56 | 115 |
| 211 | B-57 | 145 |
| 212 | B-58 | 100 |
| 213 | B-59 | 130 |
| 214 | B-60 | 110 |
| 215 | B-61 | 90 |
| 216 | B-62 | 120 |
| 217 | B-63 | 140 |
| 218 | B-64 | 130 |
| 219 | B-65 | 125 |
| 220 | B-66 | 90 |

TABLE 3-continued

| Example | Compound | Gel time (Sec) |
|---|---|---|
| Comparative Example 4 | H-4 | 600 |
| 5 | H-5 | Not gelated |
| 6 | H-6 | 400 |

The results in Tables 2 and 3 reveal that the photobase generator according to the present invention has higher sensitivity to light compared with photobase generators for comparison, and is useful as a photobase generator.

INDUSTRIAL APPLICABILITY

The photobase generator according to the present invention is suitably used for a paint, a coating agent, various kinds of covering materials (a material for hard coat, a stain-resistant covering material, a defogging covering material, a corrosion-resistant covering material, an optical fiber and the like), a backside treating agent for a pressure-sensitive adhesive tape, a release coating material of a releasable sheet for a pressure-sensitive adhesive label (release paper, a release plastic film, release metal foil and the like), a printing plate, dental materials (a dental formulation, a dental composite), an ink, an inkjet ink, a positive type resist (a connecting terminal, wiring pattern formation, or the like in the production of electronic components such as a circuit board, CSP and an MEMS element), a resist film, a liquid resist, a negative type resist (a permanent film material such as an interlayer insulating film, a flattening film and a surface protective film such as a semiconductor element and a transparent electrode for FPD (ITO, IZO, GZO) and the like), a resist for MEMS, a positive type photosensitive material, a negative type photosensitive material, various kinds of adhesives (temporary fixing agents for various kinds of electronic components, an adhesive for HDD, an adhesive for pickup lens, an adhesive for a functional film for FPD (a deflection plate, an antireflection film or the like), insulator films for circuit formation and for semiconductor sealing, an anisotropic conductive adhesive (ACA), film (ACF) or paste (ACP), and the like), a resin for holography, FPD materials (a color filter, a black matrix, a partition wall material, a photospacer, a rib, an oriented film for liquid crystal, a sealing agent for FPD and the like), an optical member, molding materials (ones for building materials, an optical component, a lens), a casting material, putty, an impregnant for glass fiber, a filling material, a sealing material, a flip chip, a chip sealing material for COF or the like, a sealing material for package such as CSP and BGA, an optical semiconductor (LED) sealing material, an optical waveguide material, a nanoimprint material, materials for photofabrication and for micro-photofabrication, and the like while utilizing a base generated by photoirradiation.

The invention claimed is:
1. A photobase generator, comprising a salt represented by general formula (3):

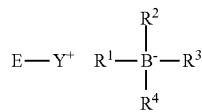

(3)

[wherein in general formula (3), $R^1$ to $R^4$ independently represent a group represented by general formula (2) below, an alkyl group having 1 to 18 carbon atoms or Ar, wherein at least one of $R^1$ to $R^4$ represents a group represented by general formula (2) below, Ar represents an aryl group having 6 to 14 carbon atoms (excluding carbon atoms contained in a substituent as mentioned below), some of hydrogen atoms in the aryl group may be independently substituted by an alkyl group having 1 to 18 carbon atoms, an alkenyl group having 2 to 18 carbon atoms, an alkynyl group having 2 to 18 carbon atoms, an aryl group having 6 to 14 carbon atoms, a nitro group, a hydroxyl group, a cyano group, an alkoxy group or aryloxy group represented by —$OR^{39}$, an acyl group represented by $R^{40}CO$—, an acyloxy group represented by $R^{41}COO$—, an alkylthio group or arylthio group represented by —$SR^{42}$, an amino group represented by —$NR^{43}R^{44}$, or a halogen atom, $R^{39}$ to $R^{42}$ independently represent an alkyl group having 1 to 8 carbon atoms or an aryl group having 6 to 14 carbon atoms, and $R^{43}$ and $R^{44}$ independently represent a hydrogen atom, an alkyl group having 1 to 8 carbon atoms or an aryl group having 6 to 14 carbon atoms; in formula (2), (D) represents a divalent group having at least one bond through which a boron element is bonded, and $Ar^1$ is the same as the above-mentioned Ar; $Y^+$ represents an ammonio group represented by any one of general formulas (4) to (6) and (8) below; in formula (4), $R^5$ to $R^8$ independently represent a hydrogen atom, an alkyl group having 1 to 18 carbon atoms, an alkenyl group having 2 to 18 carbon atoms or an aryl group having 6 to 14 carbon atoms, and may be bonded to one another to form a ring structure; in formula (5), $R^9$ to $R^{15}$ independently represent a hydrogen atom, an alkyl group having 1 to 18 carbon atoms, an alkenyl group having 2 to 18 carbon atoms or an aryl group having 6 to 14 carbon atoms, and may be bonded to one another to form a ring structure, and p represents an integer of 0 to 6; in formula (6), $R^{16}$ to $R^{18}$ independently represent a hydrogen atom, an alkyl group having 1 to 18 carbon atoms or an aryl group having 6 to 14 carbon atoms, and may be bonded to one another to form a ring structure, R' represents a group represented by general formula (7), and q represents an integer of 0 to 3; in formula (7), $R^{19}$ to $R^{24}$ independently represent a hydrogen atom, an alkyl group having 1 to 18 carbon atoms or an aryl group having 6 to 14 carbon atoms, and may be bonded to one another to form a ring structure; in formula (8), $R^{25}$ to $R^{27}$ independently represent a hydrogen atom, an alkyl group having 1 to 18 carbon atoms or an aryl group having 6 to 14 carbon atoms, and may be bonded to one another to form a ring structure; and E represents a group represented by general formula (9) below, $R^{28}$ to $R^{32}$ independently represent hydrogen atom, an alkyl group having 1 to 18 carbon atoms, a nitro group, a hydroxyl group, a cyano group, an alkoxy group represented by —$OR^{39}$, an acyl group represented by $R^{40}CO$—, an acyloxy group represented by $R^{41}COO$—, an alkylthio group represented by —$SR^{42}$, an amino group represented by —$NR^{43}R^{44}$ or a halogen atom, $R^{28}$ to $R^{32}$ may be the same as or different from one another and may be bonded to one another to form a ring structure, in general formula (9), (G) represents a divalent group represented by general formula (10) or general formula (11), and $R^{33}$ to $R^{36}$ independently represent a hydrogen atom, an alkyl group having 1 to 18 carbon atoms or an aryl group having 6 to 14 carbon atoms, and may be the same as or different from one another,]

-(D)-Ar¹ (2)

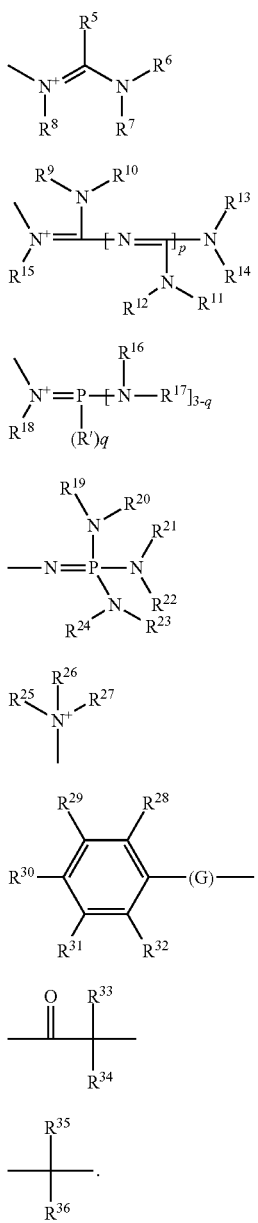

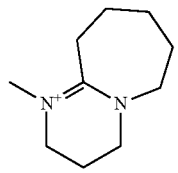

(12)

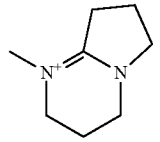

(13)

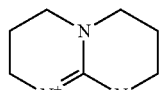

(14)

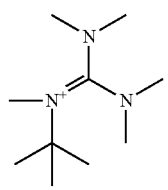

(15)

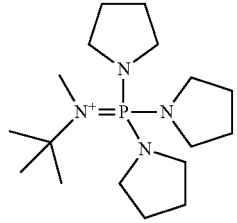

(16)

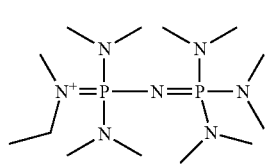

(17)

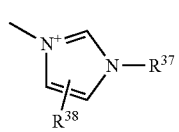

(18)

[wherein in formula (18), $R^{37}$ represents an alkyl group having 1 to 18 carbon atoms, an alkenyl group having 2 to 18 carbon atoms or an aryl group having 6 to 14 carbon atoms, $R^{38}$ represents an alkyl group having 1 to 18 carbon atoms, and $R^{37}$ and $R^{38}$ may be bonded to each other to form a ring structure].

2. The photobase generator according to claim 1, wherein an absorption wavelength which Ar as one of $R^1$ to $R^4$ in general formula (1) has and an absorption wavelength which $Ar^1$ in general formula (2) has satisfy an inequality of $Ar<Ar^1$.

3. The photobase generator according to claim 1, wherein Ar as one of $R^1$ to $R^4$ in general formula (1) represents a phenyl group or a naphthyl group.

4. The photobase generator according to claim 1, wherein $Y^+$ in general formula (3) represents an ammonio group selected from the group of general formulas (12) to (18) below:

5. A photocurable composition, comprising the photobase generator according to claim 1 and a basic reactive compound.

6. A cured product obtained by curing the photocurable composition according to claim 5.

7. The photobase generator according to claim 1, wherein $Y^+$ represents an ammonio group represented by any one of general formulas (4) to (6).

8. The photobase generator according to claim 1, wherein the divalent group of the (D) is selected from an ether, a sulfide, a ketone, an imine, a sulfoxide, a sulfone, an amide, an imide, a carboxylic acid ester, a thiocarboxylic acid ester, a carbonate ester, an acid anhydride, a urea, a thiourea, an acetal, a thioacetal, a carbodiimide, a carbamoyl, a thiocarbamoyl, a silylene and a siloxy, an alkylene having 1 to 18 carbon atoms which may have a substituent, an alkenylene having 2 to 18 carbon atoms, an alkynylene having 2 to 18 carbon atoms, and an arylene having 6 to 14 carbon atoms which may contain a hetero atom.

9. The photobase generator according to claim 1, wherein the divalent group of the (D) is selected from an alkylene having 1 to 18 carbon atoms, an arylene with 6 to 14 carbon atoms which may contain a hetero atom, ether, a sulfide and a carboxylic acid ester.

* * * * *